*(12)* United States Patent
Dyer et al.

(10) Patent No.: US 11,788,026 B2
(45) Date of Patent: Oct. 17, 2023

(54) HYDRAULIC FLUID

(71) Applicant: Afton Chemical Corporation, Richmond, VA (US)

(72) Inventors: Helen Dyer, Bracknell (GB); Jason Bell, Powhatan, VA (US)

(73) Assignee: AFTON CHEMICAL CORPORATION, Richmond, VA (US)

( * ) Notice: Subject to any disclaimer, the term of this patent is extended or adjusted under 35 U.S.C. 154(b) by 0 days.

(21) Appl. No.: 17/387,440

(22) Filed: Jul. 28, 2021

(65) Prior Publication Data

US 2023/0076125 A1 Mar. 9, 2023

(51) Int. Cl.
*C10M 169/04* (2006.01)
*C07D 249/18* (2006.01)
(Continued)

(52) U.S. Cl.
CPC ....... *C10M 169/044* (2013.01); *C07D 249/18* (2013.01); *C10M 133/44* (2013.01);
(Continued)

(58) Field of Classification Search
CPC .......... C10M 169/044; C10M 137/105; C10M 135/10; C10M 141/10; C10M 149/02;
(Continued)

(56) References Cited

U.S. PATENT DOCUMENTS 4,522,785 A 6/1985 D'Errico
5,032,300 A 7/1991 O'Neil
(Continued)

FOREIGN PATENT DOCUMENTS

CA 1077047 * 5/1980
CA 2442697 A1 10/2002
(Continued)

OTHER PUBLICATIONS

Saji, Viswanathan S., "A Review of Recent Patents in Corrosion Inhibitors," Recent Patents on Corrosion Science, 2010, 2, pp. 6-12.
(Continued)

*Primary Examiner* — Cephia D Toomer
(74) *Attorney, Agent, or Firm* — Honigman LLP

(57) ABSTRACT

The present invention provides a hydraulic fluid comprising:
(a) 40 to 2000 ppm by weight in terms of nitrogen content of a corrosion inhibiting agent which is one or more compounds of formula (I):

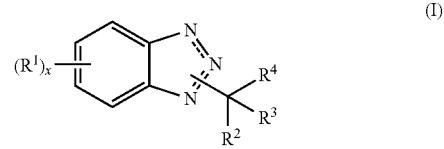

and/or tribologically acceptable salts thereof, wherein in formula (I):
each $R^1$ is independently a hydrocarbyl group comprising 1 to 10 carbon atoms,
x is 0 to 4,
each of $R^2$ and $R^3$ is independently hydrogen or a hydrocarbyl group comprising 1 to 20 carbon atoms,
$R^4$ is $-NR^5R^6$ or $-OR^7$,
each of $R^5$ and $R^6$ is independently an aryl group comprising 6 to 14 carbon atoms, optionally substituted with one or more hydrocarbyl groups comprising 1 to 20 carbon atoms,
$R^7$ is a hydrocarbyl group comprising 1 to 20 carbon atoms, and
(Continued)

in each of said hydrocarbyl groups containing 2 or more carbon atoms, the carbon chain may, independently, optionally be interrupted by one or more ether groups;
(b) 0.1 to 1% by weight of an ashless dispersant; and
(c) a major amount of a base oil.

11 Claims, 4 Drawing Sheets

(51) Int. Cl.
| | |
|---|---|
| C10M 133/44 | (2006.01) |
| C10M 135/10 | (2006.01) |
| C10M 137/10 | (2006.01) |
| C10M 141/10 | (2006.01) |
| C10M 149/02 | (2006.01) |
| C10M 161/00 | (2006.01) |
| C10N 40/08 | (2006.01) |

(52) U.S. Cl.
CPC ...... *C10M 135/10* (2013.01); *C10M 137/105* (2013.01); *C10M 141/10* (2013.01); *C10M 149/02* (2013.01); *C10M 161/00* (2013.01); C10M 2203/003 (2013.01); C10M 2215/30 (2013.01); C10M 2217/06 (2013.01); C10M 2219/044 (2013.01); C10M 2223/047 (2013.01); C10N 2040/08 (2013.01)

(58) Field of Classification Search
CPC .............. C10M 161/00; C10M 133/44; C10M 2203/003; C10M 2215/30; C10M 2223/047; C10M 2219/044; C10M 2217/06; C07D 249/18; C10N 2070/02; C10N 2040/08; C10N 2030/12; C10N 2030/04; C10N 2030/10; C10N 2030/06
See application file for complete search history.

(56) References Cited

U.S. PATENT DOCUMENTS

| | | | |
|---|---|---|---|
| 5,137,980 A | * | 8/1992 | DeGonia ............... C10L 1/221 |
| | | | 525/327.7 |
| 5,714,442 A | | 2/1998 | Wolf |
| 6,406,643 B2 | | 6/2002 | Linden et al. |
| 6,436,882 B1 | | 8/2002 | Rizvi |
| 2003/0134753 A1 | * | 7/2003 | Stunkel ............... C10M 141/08 |
| | | | 508/281 |
| 2008/0029430 A1 | | 2/2008 | Loh et al. |
| 2009/0105102 A1 | | 4/2009 | Rapenne-Jacob et al. |
| 2010/0130394 A1 | | 5/2010 | Tsubouchi |
| 2011/0212864 A1 | | 9/2011 | Rapenne-Jacob et al. |
| 2014/0342957 A1 | | 11/2014 | Donnelly et al. |
| 2015/0133352 A1 | | 5/2015 | Esche et al. |
| 2016/0122680 A1 | | 5/2016 | Watts et al. |

FOREIGN PATENT DOCUMENTS

| | | | |
|---|---|---|---|
| EP | 0365476 | A1 | 4/1990 |
| EP | 0821053 | * | 1/1998 |
| EP | 0 905 221 | A1 | 3/1999 |
| GB | 867181 | A | 5/1961 |
| GB | 1466558 | * | 3/1977 |
| JP | 2005-509732 | A | 4/2005 |
| WO | 9935219 | A1 | 7/1999 |
| WO | 0046325 | A1 | 8/2000 |
| WO | 2006053858 | A1 | 5/2006 |
| WO | 2010021643 | A2 | 2/2010 |
| WO | 2014078702 | A1 | 5/2014 |

OTHER PUBLICATIONS

The extended European Search Report issued in the European Patent Application No. 22187424.1-1110 dated Nov. 25, 2022; 7 pages.

* cited by examiner

HYDRAULIC FLUID

FIELD

The present invention relates to the provision of hydraulic fluids with an improved balance of desirable properties, in particular in relation to the functional properties of the fluid and its compatibility with fluoropolymer seals and yellow metal (e.g. copper) components.

BACKGROUND

It is desirable for hydraulic fluids to exhibit good power transmission, but it is also desirable for them to exhibit other important characteristics such as thermal stability, rust inhibition, and anti-wear performance. Additives may thus be added to hydraulic fluids in order to help achieve satisfactory performance in various different respects.

However, there can be a trade off when it comes to the achievement of multiple different desirable properties. For instance, anti-wear additives may be added to improve pump performance in some situations, but not all anti-wear additives are thermally stable, so at higher concentrations they may contribute to the formation of sludge or varnish, and/or may break down to form acidic species that can lead to the blockage of filters.

Meanwhile, the goals of improving the reliability of machinery and minimising maintenance requirements mean it is desirable for hydraulic fluids to remain functional for longer and longer time periods. It is advantageous not only for hydraulic fluids to be able to function effectively for extended periods, but also for them to have good compatibility with the materials they contact.

For instance, compatibility is desired between a hydraulic fluid and any metal surfaces it may contact, including surfaces containing so called yellow metals, such as copper. In particular, it is desirable to avoid or minimise the corrosion/dissolution of such metals. One past approach to tackling this has been to employ 0.05-1.0 wt % of a corrosion inhibiting additive with a typical chemical structure selected from carboxylic acids, benzotriazole, metal sulphonates and alkylated carboxylic acids (Hydraulic Fluids, 1996, P.K.B Hodges). For instance, carboxylic acids described for this purpose include both aryl and aliphatic carboxylic acids—see e.g. WO1999035219, while GB867181 describes the use of benzotriazole, preferably in an amount of 0.25% by weight. Derivatives of benzotriazole have also been suggested, though, such as the product sold under the trade name Irgamet® 39, and also tolyltriazole (see e.g. U.S. Pat. No. 6,406,643). The Irgamet® 39 corrosion inhibitor has the structure set out below.

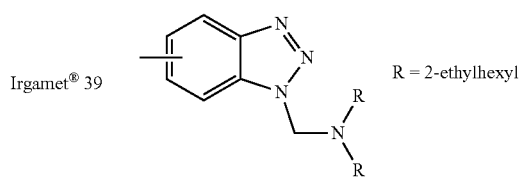

Irgamet® 39    R = 2-ethylhexyl

Compounds with this dialkylaminomethyl aromatic triazole structure have been reported as providing excellent corrosion inhibiting properties even in acidic environments (see e.g. U.S. Pat. No. 4,522,785). They also have the benefit of being a liquid at room temperature, in contrast to e.g. tolyltriazole which is a solid at room temperature.

1H-1,2,4-triazole has been reported as being preferred to benzotriazole compounds on the basis that it offers comparable corrosion inhibition but provides a coating-free metal surface and reduced sediment formation (CA2442697). Combinations of 1H-1,2,4-triazole with benzotriazole derivatives have also been described (WO0046325), as have various triazole derivatives and also imidazole derivatives (see e.g. WO2010021643), and the use of benzotriazole compounds and/or thiadiazole compounds in amounts of 0.1 to 5 wt % (see e.g. US2010130394).

Other more recently described corrosion inhibiting substances in relation more generally to lubricants and hydraulic fluids include (i) P- and S-free organotungstates; (ii) oil soluble 2,5-dimercapto-1,3,4-thiadiazole or hydrocarbyl-substituted 2,5-dimercapto-1,3,4-thiadiazole derivatives; (iii) Na or Ca salts of dinonylnaphthalene-sulfonic acid; (iv) a hydrocarbyl-substituted 1,2,4-triazole; and (v) a combination of lanthanum oxide, triglycerides of higher carboxylic acids, alkylbenzenesulfonic acid, alkanolamine, lanthanum nitrate and organic solvent (see e.g. "A Review on Recent Patents in Corrosion Inhibitors", Viswanathan S. Saji, Recent Patents on Corrosion Science, 2010, 2, 6-12).

Another consideration in relation to the compatibility of a hydraulic fluid with the materials with which it comes into contact is its compatibility with the polymer materials which are used in seals, particularly in hydraulic systems. Seals have previously been made from materials such as nitrilic rubbers and their hydrogenated analogues, acrylates and vinyl-modified acrylic polymers, with contacting fluids being provided with seal swelling agents such as phthalate esters, sulfolane derivatives and naphthenic oils to swell and soften the seals to facilitate effective operation. However, more recently some systems have moved to using seals manufactured from materials such as fluoropolymers, including the subset of fluoropolymers that may be designated "FKM". Such fluoropolymer seals can offer advantages but may also be vulnerable to degradation, e.g. via de-polymerisation or cross-linking reactions. In particular, there is the potential for some of the different types of additive that may be included in hydraulic fluids to cause or encourage such degradative reactions. For instance, FKM fluoropolymers do not always show good resistance to ethers, ketones, esters, and amines, or to hydraulic fluids based on phosphate esters. Thus, there can be a trade-off between the potentially competing aims of providing good functionality and good seal compatibility. Achieving good seal compatibility without compromising on functionality can therefore be difficult.

Some ways of improving fluoropolymer seal compatibility have been described in the context of other fluids. For instance, one approach described in WO2014078702 in connection with lubricant compositions involves adding epoxide compounds such as the one depicted below in combination with an amine compound having a total base number of at least 80 mg KOH/g (when tested according to ASTM D4739).

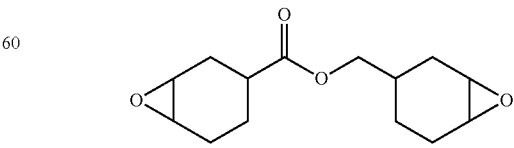

However, introducing extra agents in order to improve seal compatibility is not an ideal solution, not least because it can give rise to complications. For example, in WO2014178702 it is noted that epoxide compounds such as the one depicted above have the potential to react with other additives such as acids, amines, anyhydrides, triazoles, and/or oxides.

More recently, US2016/0122680 has reported that the seal compatibility of power transmitting fluids containing a dispersant, an anti-wear agent and an antioxidant together with either of two different common commercial friction modifiers (one made by reacting tetraethylene pentamine with iso-stearic acid, the other made by reacting tetraethylene pentamine with iso-octadecenylsuccinic anhydride) may be improved by replacing the commercial friction modifier with an alternative friction modifier that is made by reacting (a) iso-stearic acid or oleic acid, with (b) 400 molecular weight polyethylene glycol or ETHOMEEN® C-15 (said to comprise polyalkoxylated alkyl amine compounds), in the presence of an esterification catalyst. However, there remains a need for improving the seal compatibility of other types of fluid.

SUMMARY OF THE INVENTION

The present invention is based on the surprising finding that the use of a small amount of a certain type of corrosion inhibiting agent can enable the provision of an unexpectedly advantageous balance of properties, in particular in relation to the potentially competing goals of good functionality (such as good corrosion inhibition) and good fluoropolymer seal compatibility. Thus, the corrosion inhibiting agent defined herein has been found to provide robust corrosion inhibition at very low concentrations, in particular when also combined with certain other additives. Among the benefits of this are that it enables any potential negative impact the corrosion inhibiting agent may have on fluoropolymer seals to be minimised. Further, the minimal effect that the corrosion inhibiting agent has on the seals (i.e. its good seal compatibility) makes it possible to raise the levels of other additives that might otherwise have been avoided or used relatively sparingly due to concern that they may have a degradative effect on fluoropolymer seals, thus enabling the achievement of new and improved levels of functionality for hydraulic fluids with good fluoropolymer seal compatibility.

The corrosion inhibiting agent for use according to the invention is one or more compounds of formula (I):

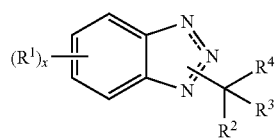

(I)

and/or tribologically acceptable salts thereof, wherein in formula (I):
each $R^1$ is independently a hydrocarbyl group comprising 1 to 10 carbon atoms,
x is 0 to 4,
each of $R^2$ and $R^3$ is independently hydrogen or a hydrocarbyl group comprising 1 to 20 carbon atoms,
$R^4$ is —$NR^5R^6$ or —$OR^7$,
each of $R^5$ and $R^6$ is independently an aryl group comprising 6 to 14 carbon atoms, optionally substituted with one or more hydrocarbyl groups comprising 1 to 20 carbon atoms,
$R^7$ is a hydrocarbyl group comprising 1 to 20 carbon atoms, and
in each of said hydrocarbyl groups containing 2 or more carbon atoms, the carbon chain may, independently, optionally be interrupted by one or more ether groups.

The finding that using very low quantities of the above corrosion inhibiting agent can enable the achievement of excellent performance in terms of both fluoropolymer seal compatibility and the various other functional requirements of a hydraulic fluid is particularly striking when compared to the balance of properties that can be achieved using the known corrosion inhibitor Irgamet® 39 (the structure of which is set out above in the Background section).

DETAILED DESCRIPTION OF THE INVENTION

Figure 1:
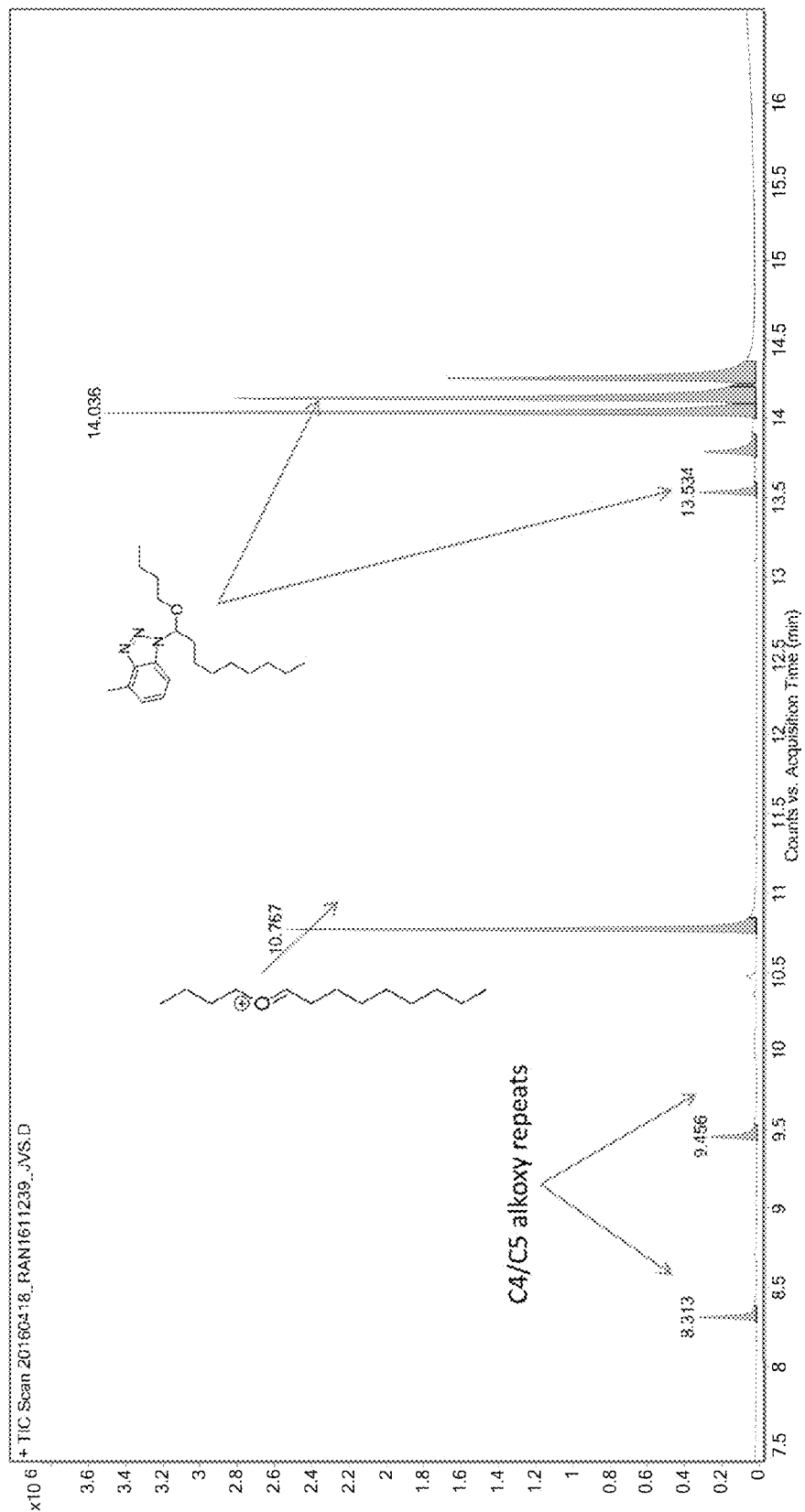
FIG. 1 is a GC-MS plot of the reaction product of Example 1.

The present invention provides a hydraulic fluid comprising:
(a) 40 to 2000 ppm by weight in terms of nitrogen content of a corrosion inhibiting agent which is one or more compounds of formula (I):

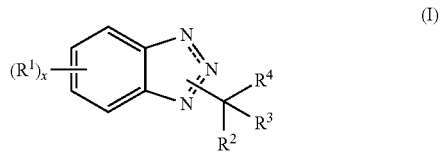

(I)

and/or tribologically acceptable salts thereof, wherein in formula (I):
each $R^1$ is independently a hydrocarbyl group comprising 1 to 10 carbon atoms,
x is 0 to 4,
each of $R^2$ and $R^3$ is independently hydrogen or a hydrocarbyl group comprising 1 to 20 carbon atoms,
$R^4$ is —$NR^5R^6$ or —$OR^7$,
each of $R^5$ and $R^6$ is independently an aryl group comprising 6 to 14 carbon atoms, optionally substituted with one or more hydrocarbyl groups comprising 1 to 20 carbon atoms,
$R^7$ is a hydrocarbyl group comprising 1 to 20 carbon atoms, and
in each of said hydrocarbyl groups containing 2 or more carbon atoms, the carbon chain may, independently, optionally be interrupted by one or more ether groups;
(b) 0.1 to 1% by weight of an ashless nitrogen-containing dispersant; and
(c) a major amount of a base oil.

The present invention also provides an additive concentrate comprising:

(a) 2.0 to 20% by weight of a corrosion inhibiting agent which is one or more compounds of formula (I) as defined herein;
(b) 11 to 50% by weight (preferably 11 to 45% by weight) of an ashless nitrogen-containing dispersant; and optionally
(c) a diluent oil.

Some compounds and salts of formula (I) above are believed to be novel. Thus, the present invention also provides a compound of formula (II):

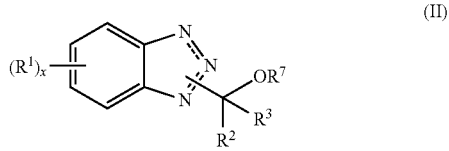

(II)

or a tribologically acceptable salt thereof, wherein in formula (II):
  each $R^1$ is independently a hydrocarbyl group comprising 1 to 10 carbon atoms,
  x is 0 to 4,
  each of $R^1$ and $R^3$ is independently hydrogen or a hydrocarbyl group comprising 1 to 20 carbon atoms,
  $R^7$ is a group comprising 1 to 20 carbon atoms, and
  in each of said hydrocarbyl groups containing 2 or more carbon atoms, the carbon chain may, independently, optionally be interrupted by one or more ether groups,
provided that either
(a) between them $R^2$ and $R^3$ have at least 7 carbon atoms and $R^7$ has at least 2 carbon atoms,
(b) between them $R^2$ and $R^3$ have at least 5 carbon atoms and $R^7$ has at least 2 carbon atoms and is not a cycloalkyl group,
(c) neither of $R^2$ and $R^3$ is H, and between them $R^2$ and $R^3$ have at least 3 carbon atoms,
(d) x is 1 to 4, $R^1$ has at least 2 carbon atoms, and either (i) $R^7$ has at least 2 carbon atoms, (ii) neither of $R^2$ and $R^3$ is H, or (iii) between them $R^2$ and $R^3$ have at least 3 carbon atoms, or
(e) x is 2 to 4.

The present invention also provides a hydraulic system comprising at least one fluoropolymer seal and a hydraulic fluid of the invention as defined herein which comes into contact with the seal.

The present invention also provides the use of a hydraulic fluid of the invention as defined herein as a power transmitting fluid.

The present invention also provides the use, in a hydraulic fluid, to improve fluoropolymer seal compatibility, or to preserve the integrity of one or more fluoropolymer seals which come into contact with said hydraulic fluid, of 40 to 200 ppm by weight in terms of nitrogen of:
  a corrosion inhibiting agent as defined herein, or
  a compound or salt of the invention as defined herein.

The present invention also provides the use, in a hydraulic fluid, to inhibit corrosion while also (a) improving fluoropolymer seal compatibility, or (b) preserving the integrity of one or more fluoropolymer seals which come into contact with said hydraulic fluid, of 40 to 200 ppm by weight in terms of nitrogen of:
  one or more compounds of formula (I) and/or tribologically acceptable salts thereof as defined herein, or
  a compound or salt of the invention as defined herein.

Component (a): A Compound of Formula (I) or a Tribologically Acceptable Salt Thereof The hydraulic fluid of the present invention comprises 40 ppm to 2000 ppm by weight in terms of nitrogen (based on the total weight of the hydraulic fluid) of a corrosion inhibiting agent which is one or more compounds of formula (I) as defined above and/or tribologically acceptable salts thereof.

In this regard, for the avoidance of doubt, the hydraulic fluid may comprise more than one different type of compound of formula (I) and/or salt thereof, provided that the total amount of said compounds/salts does not exceed the upper limit of 2000 ppm by weight in terms of nitrogen content. In other words, component (a) may be one or more compounds of formula (I) and/or tribologically acceptable salts thereof (wherein 40 to 2000 ppm refers to the total concentration of all such compounds and/or salts in terms of their nitrogen content). In this regard, the term "one or more" preferably means one, two, or three, and more preferably it means one or two. Typically, though, it is only necessary to include one compound of formula (I) and/or tribologically acceptable salt thereof.

Preferably in formula (I), each $R^1$ is independently a straight or branched alkyl group or an aryl group such as phenyl. More preferably each $R^1$ is independently a straight or branched alkyl group.

Preferably, each $R^1$ independently comprises 1 to 8 carbon atoms, more preferably 1 to 6 carbon atoms, and yet more preferably 1 to 4 carbon atoms. Preferred examples for $R^1$ are alkyl groups such as methyl, ethyl, n-propyl, i-propyl, n-butyl, i-butyl, and t-butyl. Methyl and ethyl are particularly preferred, and methyl most preferred.

The upper limit for the moiety x is preferably 3, more preferably 2. The lower limit for x is preferably 1. It is particularly preferred for x to be 0 or 1. Most preferably, x is 1.

When $R^4$ is $NR^5R^6$, $R^2$ is preferably hydrogen or a straight or branched alkyl group or an aryl group such as phenyl. More preferably $R^2$ is hydrogen or a straight or branched alkyl group. Most preferably $R^2$ is hydrogen.

When $R^4$ is —$NR^5R^6$ and $R^2$ is a hydrocarbyl group containing 1 to 20 carbon atoms, $R^2$ preferably comprises 1 to 8 carbon atoms, more preferably 1 to 6 carbon atoms, and yet more preferably 1 to 4 carbon atoms. Preferred examples for $R^2$ in this regard are alkyl groups such as methyl, ethyl, n-propyl, i-propyl, n-butyl, i-butyl, and t-butyl, with methyl and ethyl being particularly preferred, and methyl most preferred.

When $R^4$ is —$OR^7$, $R^2$ is preferably hydrogen or a straight or branched alkyl group or an aryl group such as phenyl. More preferably $R^2$ is a straight or branched alkyl group.

When $R^4$ is —$OR^7$ and $R^2$ is a hydrocarbyl group containing 1 to 20 carbon atoms, $R^2$ preferably comprises 2 to 16 carbon atoms, more preferably 4 to 12 carbon atoms, and yet more preferably 6 to 10 carbon atoms. Preferred examples for $R^2$ in this regard are alkyl groups such as the straight and branched forms of hexyl, heptyl, octyl, nonyl and decyl, with n-octyl most preferred.

When $R^4$ is —$OR^7$ the compound of formula (I) is preferably a compound of formula (II) as defined further below.

$R^3$ is preferably hydrogen or a straight or branched alkyl group or an aryl group such as phenyl. More preferably $R^3$ is hydrogen or a straight or branched alkyl group. Most preferably $R^3$ is hydrogen.

When $R^3$ is a hydrocarbyl group containing 1 to 20 carbon atoms, it preferably comprises 1 to 8 carbon atoms, more preferably 1 to 6 carbon atoms, and yet more preferably 1 to 4 carbon atoms. Preferred examples for $R^3$ in this regard are alkyl groups such as methyl, ethyl, n-propyl, i-propyl, n-butyl, i-butyl, and t-butyl, with methyl and ethyl being particularly preferred, and methyl most preferred.

Preferably, each of $R^5$ and $R^6$ is independently an aryl group substituted with one or more hydrocarbyl groups. More preferably, the aryl group of each of $R^5$ and $R^6$ independently is substituted with one, two or three hydrocarbyl groups, yet more preferably one or two hydrocarbyl groups, and most preferably one hydrocarbyl group.

Preferably the aryl group of each of $R^5$ and $R^6$ independently comprises 6 to 10 carbon atoms, and most preferably 6 carbon atoms. When the aryl group of each of $R^5$ and $R^6$ independently is substituted with one or more hydrocarbyl groups, each hydrocarbyl group independently preferably comprises 2 to 16 carbon atoms, more preferably 4 to 12 carbon atoms, and yet more preferably 6 to 10 carbon atoms. Preferred examples for the hydrocarbyl groups in this regard are alkyl groups such as the straight and branched forms of hexyl, heptyl, octyl, nonyl and decyl, with n-octyl most preferred.

Preferably, each of $R^5$ and $R^6$ is independently a phenyl group substituted with one or more hydrocarbyl groups (typically alkyl groups), said hydrocarbyl groups containing 6 to 10 carbon atoms. Preferably the hydrocarbyl groups (which typically are alkyl groups) are located in the para position.

Preferably, $R^7$ is a straight or branched alkyl group or an aryl group such as phenyl. More preferably $R^7$ is a straight or branched alkyl group.

Preferably, $R^7$ comprises 1 to 10 carbon atoms, more preferably 2 to 8 carbon atoms, and yet more preferably 3 to 6 carbon atoms. Preferred examples for $R^7$ are alkyl groups such as the straight and branched forms of propyl, butyl, pentyl and hexyl, with n-butyl most preferred.

In a particularly preferred embodiment, x is 0 or 1, $R^1$ is a straight or branched alkyl group comprising 1 to 4 carbon atoms such as methyl or ethyl (typically methyl), $R^1$ is hydrogen or a straight or branched alkyl group comprising 1 to 4 carbon atoms such as methyl or ethyl (typically $R^1$ is hydrogen), $R^3$ is hydrogen or a straight or branched alkyl group comprising 1 to 4 carbon atoms such as methyl or ethyl (typically $R^3$ is hydrogen), $R^4$ is $-NR^5R^6$, $R^5$ is a phenyl group substituted with a hydrocarbyl group comprising 6 to 10 carbon atoms (typically n-octyl), and $R^6$ is a phenyl group substituted with a hydrocarbyl group comprising 6 to 10 carbon atoms (typically n-octyl). More preferably in this regard, x is 1. It is also preferred for the hydrocarbyl group comprising 6 to 10 carbon atoms to be in the para position.

In another particularly preferred embodiment, x is 0 or 1, $R^1$ is a straight or branched alkyl group comprising 1 to 4 carbon atoms such as methyl or ethyl (typically methyl), $R^2$ is a straight or branched alkyl group comprising 4 to 12 carbon atoms and preferably 6 to 10 carbon atoms (typically n-octyl), $R^3$ is hydrogen or a straight or branched alkyl group comprising 1 to 4 carbon atoms such as methyl or ethyl (typically $R^3$ is hydrogen), $R^4$ is $-OR^7$, and $R^7$ is a straight or branched alkyl group comprising 2 to 8 carbon atoms and preferably 3 to 6 carbon atoms (typically n-butyl). More preferably in this regard, x is 1.

Examples of preferred compounds of formula (I) are Compound 1 and Compound 2.

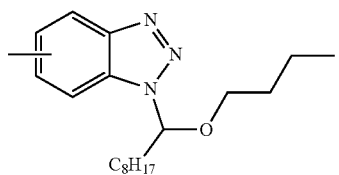

Compound 1

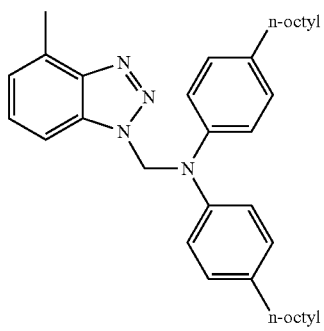

Compound 2

Some compounds and salts suitable for use as component (a) are known and are generally available commercially and/or can be prepared by well-known methods. For instance, compound 2 is available in diluted form as the commercial product Vanlube® 887.

The concentration of the corrosion inhibitor in the hydraulic fluid is from 40 ppm to 2000 ppm by weight in terms of nitrogen content (in the overall hydraulic fluid). The amount in terms of nitrogen content is preferably at least 45 ppm, such as at least 50 ppm, at least 55 ppm, at least 60 ppm, at least 65 ppm, at least 70 ppm, at least 75 ppm or at least 80 ppm. The upper limit for the amount in terms of nitrogen content is preferably at most 1500 ppm, such as at most 1000 ppm, at most 800 ppm, at most 600 ppm, at most 400 ppm, or at most 200 ppm. In some embodiments, the amount is preferably at most 190 ppm, such as at most 180 ppm, at most 170 ppm, at most 160 ppm, at most 150 ppm, at most 140 ppm, at most 130 ppm, or at most 120 ppm. Examples of preferred ranges are 50 to 140 ppm, 60 to 130 ppm and 70 to 120 ppm.

The amount of the corrosion inhibitor in the hydraulic fluid (i.e. not in terms of nitrogen content) may vary depending on the identity of x, $R^1$, $R^2$, $R^3$, $R^4$, $R^5$, $R^6$ and $R^7$. Typically the amount is at least 300 ppm, such as at least 400 ppm, at least 500 ppm, at least 600 ppm, or at least 700 ppm. The upper limit for the amount may be (e.g.) up to 4000 ppm, up to 3500 ppm, up to 3000 ppm, up to 2500 ppm, up to 2000 ppm, up to 1800 ppm, up to 1600 ppm, up to 1400 ppm, or up to 1200 ppm. In some embodiments the amount is preferably up to 1000 ppm, up to 950 ppm, up to 900 ppm, up to 880 ppm or up to 860 ppm. Examples of preferred ranges are 300 to 1900 ppm, 500 to 1300 ppm and 700 to 900 ppm. The lower values for the possible upper limits are particularly relevant for embodiments when x is lower and/or when $R^1$ and $R^3$ are smaller groups, such as in (a) the embodiment wherein x is 0 or 1, $R^1$ is a straight or branched alkyl group comprising 1 to 4 carbon atoms such as methyl or ethyl (typically methyl), $R^2$ is hydrogen or a straight or branched alkyl group comprising 1 to 4 carbon atoms such as methyl or ethyl (typically $R^2$ is hydrogen), $R^3$ is hydrogen or a straight or branched alkyl group comprising 1 to 4 carbon atoms such as methyl or ethyl (typically $R^3$ is hydrogen), $R^4$ is $-NR^5R^6$, $R^5$ is a phenyl group substituted with a hydrocarbyl group comprising 6 to 10 carbon atoms (typically n-octyl), and $R^6$ is a phenyl group substituted with a hydrocarbyl group comprising 6 to 10 carbon atoms (typically n-octyl), (b) the embodiment wherein x is 0 or 1, $R^1$ is a straight or branched alkyl group comprising 1 to 4 carbon atoms such as methyl or ethyl (typically methyl), $R^2$ is a straight or branched alkyl group comprising 4 to 12 carbon atoms and preferably 6 to 10 carbon atoms (typically n-octyl), $R^3$ is hydrogen or a straight or branched alkyl group comprising 1 to 4 carbon atoms such as methyl or ethyl (typically $R^3$ is hydrogen), $R^4$ is —$OR^7$, and $R^7$ is a straight or branched alkyl group comprising 2 to 8 carbon atoms and preferably 3 to 6 carbon atoms (typically n-butyl), and (c) the embodiment wherein the compound of formula (I) is selected from Compound 1 and Compound 2.

In the hydraulic fluid of the present invention, preferably, the total content of substituted or unsubstituted benzotriazole compounds (of any kind, i.e. including compounds not embraced by formula (I)) and, if present, preferably also any substituted or unsubstituted triazole compounds is at most 5000 ppm, at most 4000 ppm, at most 3000 ppm, at most 2000 ppm, at most 1000 ppm or at most 900 ppm. In terms of nitrogen content (in the overall fluid), the total content is preferably at most 190 ppm, such as at most 180 ppm, at most 170 ppm, at most 160 ppm, at most 150 ppm, at most 140 ppm, at most 130 ppm, at most 120 ppm, or at most 110 ppm. The use of such concentration levels is useful for helping balance fluoropolymer compatibility and corrosion inhibition. Typically the total nitrogen content of substituted or unsubstituted benzotriazole compounds (and, if present, preferably also any substituted or unsubstituted triazole compounds) corresponds essentially to the concentration of compounds of formula (I).

The hydraulic fluid is preferably substantially free of any substituted or unsubstituted benzotriazole compounds other than component (a). More preferably, the hydraulic fluid is substantially free of any substituted or unsubstituted benzotriazole or triazole compounds other than component (a). Yet more preferably, the hydraulic fluid is substantially free of any corrosion inhibitors other than component (a).

Component (b): An Ashless Nitrogen-Containing Dispersant

The hydraulic fluid of the present invention comprises 0.1 to 1% by weight of an ashless nitrogen-containing dispersant.

In this regard, for the avoidance of doubt, the hydraulic fluid may comprise more than one different type of ashless nitrogen-containing dispersant, provided that the total amount of said dispersants does not exceed the upper limit of 1% by weight. In other words, component (b) may be one or more nitrogen-containing dispersants (wherein 0.1 to 1% refers to the total concentration of all such dispersants). In this regard, the term "one or more" preferably means one, two, or three, and more preferably it means one or two. Typically, though, it is only necessary to include one dispersant (although as is usual in this field, such a single dispersant will generally not be a single compound but rather a mixture of compounds).

A preferred option for the ashless nitrogen-containing dispersant is a product obtainable from the reaction of (a) an amino compound, with (b) succinic acid and/or succinic anhydride (preferably succinic anhydride) substituted by a hydrocarbyl group having a number average molecular weight of at least 300, wherein said reaction involves the formation of at least one imido, amido, amidine, and/or acyloxy ammonium linkage, and wherein the product is substituted by a hydrocarbyl group having a number average molecular weight of at least 300.

More preferably, the ashless nitrogen-containing dispersant is a product obtainable from the reaction of (a) an amino compound, with (b) succinic acid and/or succinic anhydride (preferably succinic anhydride) substituted by a hydrocarbyl group having a number average molecular weight of 500 to 5000, wherein said reaction involves the formation of at least one imido, amido, amidine, and/or acyloxy ammonium linkage, and wherein the product is substituted by a hydrocarbyl group having a number average molecular weight of 500 to 5000.

Typically the dispersant is a hydrocarbyl substituted succinimide, wherein the hydrocarbyl group has a number average molecular weight of at least 300, preferably 500 to 5000.

The hydrocarbyl group in the above embodiments for the dispersant component is preferably PIB group.

The number average molecular weight of the hydrocarbyl group (preferably a PIB group) is preferably at least 500, such as at least 700, at least 800, or at least 900. The number average molecular weight is preferably at most 5000, such as at most 4000, at most 3000, at most 2000, at most 1500 or at most 1200. Examples of preferred ranges are 700 to 4000, 700 to 3000, 800 to 2000, 800 to 1500, and 900 to 1200.

The amino compound for use in making the ashless nitrogen-containing dispersant may be a polyamine, for example a polyamine which is a polyalkylene polyamine, and/or which is a polyamine substituted by a hydroxyalkyl, heterocyclic and/or aromatic group.

Suitable polyalkylene polyamines which may also be substituted by hydroxyalkyl include compounds of formula $(R^3)_2N$—$(Z$—$N(R^3))_nR^3$, wherein each $R^3$ is independently selected from hydrogen, a hydrocarbyl group comprising 1 to 20 carbon atoms and a hydroxy-substituted hydrocarbyl group containing 1 to 20 carbon atoms, provided that at least one $R^3$ is hydrogen; n is from 1 to 10; and each Z is independently an alkylene group comprising 1 to 18 carbon atoms. Preferably each $R^3$ is independently selected from hydrogen, methyl, ethyl, propyl, isopropyl, n-butyl, i-butyl and t-butyl. Most preferably each $R^3$ is hydrogen. Z is preferably an alkylene group comprising 1 to 4 carbon atoms, more preferably ethylene—i.e. more preferably the polyalkylene polyamine is a polyethylene polyamine. The moiety n is preferably from 2 to 8, such as from 2 to 6 or from 2 to 5.

Examples of polyalkylene polyamines include ethylenediamine, diethylenetriamine, triethylenetetraamine, tetraethylenepentamine, pentaethylenehexamine, hexaethyleneheptamine, tri-(trimethylene)tetramine, 1,2-propylene diamine, and mixtures thereof. Mixtures of such polyamines also optionally including one or more further higher boiling fractions containing 8 or more nitrogen atoms may conveniently be used.

Examples of polyalkylene polyamines substituted by hydroxyalkyl include N-(2-hydroxyethyl) ethylene diamine, N,N'-bis(2-hydroxyethyl) ethylene diamine, N-(3-hydroxybutyl) tetramethylene diamine and mixtures thereof.

Heterocyclic-substituted polyamines include hydroxyalkyl-substituted polyamines wherein the polyamines are polyalkylene polyamines as described above and the heterocyclic substituent is selected from nitrogen-containing aliphatic and aromatic heterocycles, for example piperazines, imidazolines, pyrimidines, and/or morpholines.

Examples of the heterocyclic-substituted polyamines are N-2-aminoethyl piperazine, N-2 and N-3 amino propyl morpholine, N-3(dimethyl amino) propyl piperazine, 2-heptyl-3-(2-aminopropyl) imidazoline, 1,4-bis(2-aminoethyl)

piperazine, 1-(2-hydroxyethyl) piperazine, and 2-heptadecyl-1-(2-hydroxyethyl)-imidazoline.

Aromatic polyamines include phenylene diamines and naphthalene diamines.

Examples of aromatic polyamines include compounds of formula $Ar(N(R^3)_2)_y$, wherein Ar is an aromatic moiety comprising 6 to 20 carbon atoms, each $R^3$ is independently as defined above, and y is from 2 to 8.

Preferably the polyamine is selected from ethylenediamine, diethylenetriamine, triethylenetetramine, tetraethylenepentamine, pentaethylenehexamine, hexaethyleneheptamine, dimethylaminopropylamine, aminoethylethanolamine, and mixtures thereof.

The ashless nitrogen-containing dispersant may be made by reacting (a) the amino compound, with (b) succinic acid and/or succinic anhydride (preferably succinic anhydride) substituted by a hydrocarbyl group having a number average molecular weight of at least 300, at a molar ratio of (a):(b) of from 10:1 to 1:10, preferably from 5:1 to 1:5, more preferably from 2:1 to 1:2 and most preferably from 1:1 to 1:2. This type of acylation reaction is well known to those skilled in the art.

Preferably, the ashless nitrogen-containing dispersant is present in an amount of 1000 to 8000 ppm, more preferably 1500 to 8000 ppm, yet more preferably 1500 to 6000 ppm, and more preferably still 1500 to 4000 ppm by weight.

The amount of ashless nitrogen-containing dispersant is preferably at least 1600 ppm, such as at least 1700 ppm, or at least 1800 ppm by weight. The amount of ashless nitrogen-containing dispersant is preferably 3900 ppm or less, 3800 ppm by weight or less, 3700 ppm by weight or less, or 3600 ppm by weight or less. Examples of preferred ranges for the amount include 1600 to 3900 ppm, 1700 to 3800 ppm, 1700 to 3700 ppm and 1800 to 3600 ppm by weight.

Optional Metal Detergent

In a preferred embodiment, the hydraulic fluid of the present invention may further comprise up to 2000 ppm of metal detergent. More preferably, the hydraulic fluid of the present invention comprises 50 to 2000 ppm by weight of a metal detergent.

In this regard, for the avoidance of doubt, the metal detergent may comprise more than one different type of metal detergent, provided that the total amount of metal detergent (if present) does not exceed the upper limit of 2000 ppm by weight. In other words, the hydraulic fluid may further comprise one or more metal detergents. In this regard, the term "one or more" preferably means one, two, or three, and more preferably it means one or two. Typically, though, it is only necessary to include one metal detergent.

The metal detergent is preferably an alkaline earth metal detergent. More preferably, the hydraulic fluid comprises one or more alkaline earth metal detergents selected from phenate detergents, substituted benzene sulfonate detergents, and salicylate detergents, wherein the total amount of said one or more alkaline earth metal detergents is 50 to 2000 ppm by weight (based on the total weight of the hydraulic fluid).

The term substituted benzene sulfonate detergents refers to detergent compounds having a benzene sulfonate moiety wherein the benzene substituents include one or more (e.g. one, two or three, but typically one) hydrophobic groups. Preferably said hydrophobic groups are selected from hydrocarbyl groups, and more preferably they are selected from alkyl groups. Typically the substituted benzene sulfonate detergents are alkylbenzene sulfonate detergents.

Preferably the alkaline earth metal is calcium or magnesium, more preferably calcium. Thus, preferably said metal detergent is (i) a calcium detergent, (ii) a magnesium detergent, or (iii) a calcium detergent and a magnesium detergent. More preferably said metal detergent is one or more calcium detergents, such as one calcium detergent.

Preferably said metal detergent comprises an alkaline earth metal phenate (e.g. a calcium phenate). More preferably said metal detergent is a calcium phenate.

Preferably the calcium phenate is a calcium phenate having a total base number (TBN) of at least 100 mg KOH/g, such as at least 200 mg KOH/g, e.g. 200 to 300 mg KOH/g. TBN may preferably be measured by ASTM D2896.

Preferably the calcium phenate has a calcium content of 5 to 14% by weight, such as 8 to 11% by weight. Typically it is around 9.2% by weight.

The lower limit for the total amount of said metal detergent is typically 50 ppm, but preferably may be higher, e.g. 60 ppm, 70 ppm, 80 ppm, 90 ppm, or 100 ppm. The upper limit for the total amount of said one or more alkaline earth metal detergents is 2000 ppm, but preferably may be lower, e.g. 1800 ppm, 1700 ppm, 1600 ppm, 1500 ppm, 1400 ppm, 1300 ppm, 1200 ppm, 1100 ppm, 1050 ppm or 1030 ppm. Typical preferred concentration ranges are e.g. 50 to 1500 ppm, 70 to 1200 ppm, 90 to 1100 ppm, or 100 to 1030 ppm.

The lower limit for the total amount of said metal detergent may typically be 4 ppm in terms of metal content (based on the total weight of the hydraulic fluid), but preferably may be higher, e.g. 10 ppm, 20 ppm, 30 ppm, 40 ppm, 50 ppm, 60 ppm, 70 ppm, 80 ppm, 90 ppm or 100 ppm. The upper limit for the total amount of said metal detergent in terms of metal content may typically be 200 ppm, but preferably may be lower, e.g. 190 ppm, 180 ppm, 170 ppm, 160 ppm, 150 ppm, 140 ppm or 130 ppm. Typical preferred concentration ranges are e.g. 35 to 115 ppm, or 40 to 80 ppm. The content of metal may preferably be measured by ASTM D4951.

Preferably the total content of alkaline earth metal detergents, if present, is at most 1800 ppm, such as at most 1600 ppm, at most 1400 ppm, at most 1200 ppm, at most 1100 ppm, at most 1050 ppm, or at most 1030 ppm.

Preferably the hydraulic fluid of the present invention comprises 50 to 2000 ppm by weight of one or more alkaline earth metal (preferably calcium) phenates, such as 80 to 1500 ppm or 100 to 1030 ppm by weight thereof Optional Phosphorus-Containing Anti-Wear Agent The hydraulic fluid of the present invention preferably comprises a phosphorus-containing anti-wear agent, wherein the total amount of said phosphorus-containing anti-wear agent is 100 to 3000 ppm by weight (based on the total weight of the hydraulic fluid). The phosphorus-containing anti-wear agent may comprise (and preferably is) an ashless phosphate and/or an ashless phosphite.

Preferably the phosphorus-containing anti-wear agent is a phosphate. Thus, the hydraulic fluid of the present invention preferably comprises one or more phosphate anti-wear agents, wherein the total amount of said one or more phosphate anti-wear agents is 100 to 3000 ppm by weight (based on the total weight of the hydraulic fluid).

In this regard, the term "one or more" preferably means one, two, or three phosphate anti-wear agent(s), more preferably one or two phosphate anti-wear agent(s), and most preferably two phosphate anti-wear agents.

Preferably said one or more phosphate anti-wear agents is one or more dithiophosphate anti-wear agents.

Preferably the phosphate anti-wear agents are free of zinc, and more preferably they are ashless. Thus, preferably said one or more phosphate anti-wear agents is one or more ashless phosphate anti-wear agents. Typically said one or more ashless phosphate anti-wear agents is one or more organic phosphate anti-wear agents, and preferably it is one or more ashless organic dithiophosphate anti-wear agents.

Preferably said one or more phosphate anti-wear agents is one or more phosphate compounds of formula (III):

$$R^A\underset{\underset{R^B}{|}}{\overset{\overset{X^1}{\|}}{\underset{X^3}{X^2-P}}}-X^4-R^C-X^5-R^D \quad (III)$$

and/or tribologically acceptable salts thereof, wherein:
each $R^A$ and $R^B$ is independently a hydrocarbyl group comprising 1 to 20 carbon atoms
each $X^1$, $X^2$, $X^3$ and $X^4$ is independently S or O;
$R^C$ is a divalent hydrocarbyl group comprising 1 to 20 carbon atoms;
$X^5$ is —C(O)O— or —O—; and
$R^D$ is hydrogen or a hydrocarbyl group comprising 1 to 20 carbon atoms.

Preferably, each $R^A$ and $R^B$ is independently a straight or branched alkyl group or an aryl group such as phenyl. More preferably each $R^A$ and $R^B$ is independently a straight or branched alkyl group.

Preferably, each $R^A$ and $R^B$ independently comprises 1 to 12 carbon atoms, more preferably 1 to 8 carbon atoms, and yet more preferably 2 to 6 carbon atoms. Preferred examples for $R^A$ and $R^B$ are alkyl groups such as methyl, ethyl, n-propyl, i-propyl, n-butyl, i-butyl, and t-butyl. The groups i-propyl and i-butyl are particularly preferred.

$X^1$ is preferably S.
$X^2$ is preferably O.
$X^3$ is preferably O.
$X^4$ is preferably S.

Preferably, $R^C$ is a straight or branched alkylene group or an arylene (i.e. divalent aryl) group such as phenylene. More preferably $R^C$ is a straight or branched alkylene group.

Preferably, $R^C$ comprises 1 to 12 carbon atoms, more preferably 1 to 8 carbon atoms, and yet more preferably 2 to 6 carbon atoms. Preferred examples for $R^C$ are alkylene groups such as —CH$_2$—, —CH$_2$—CH$_2$—, —CH$_2$—CH$_2$—CH$_2$—, —CH(CH$_3$)—CH$_2$—, —CH$_2$—CH(CH$_3$)—, —CH$_2$—CH$_2$—CH$_2$—CH$_2$—, —CH(CH$_3$)—CH$_2$—CH$_2$—, —CH$_2$—CH(CH$_3$)—CH$_2$—, —CH$_2$—CH$_2$—CH(CH$_3$)—, —CH(CH$_3$)—CH(CH$_3$)—, —C(CH$_3$)$_2$—CH$_2$—, and —CH$_2$—C(CH$_3$)$_2$—. Of these, groups containing 2 or 3 carbon atoms are preferred, in particular —CH$_2$—CH$_2$— and —CH$_2$—CH(CH$_3$)—.

$X^5$ is preferably —C(O)O—.

In a particularly preferred embodiment, $X^1$ and $X^4$ are S, and $X^2$ and $X^3$ are O.

When $R^D$ is a hydrocarbyl group containing 1 to 20 carbon atoms, it preferably comprises 1 to 12 carbon atoms, more preferably 1 to 8 carbon atoms, and yet more preferably 2 to 6 carbon atoms.

Preferably, $R^D$ is hydrogen, a straight or branched alkyl group, or an aryl group such as phenyl. More preferably $R^D$ is hydrogen or a straight or branched alkyl group.

When $R^D$ is a straight or branched alkyl group, preferred examples for $R^D$ are methyl, ethyl, n-propyl, i-propyl, n-butyl, i-butyl, and t-butyl. Ethyl, n-propyl, and i-propyl are particularly preferred, and i-propyl most preferred.

In a particularly preferred embodiment:
each $R^A$ and $R^B$ is independently an alkyl group comprising 2 to 6 carbon atoms
$X^1$ and $X^4$ are S;
$X^2$ and $X^3$ are O;
$R^C$ is a divalent alkyl group comprising 2 to 6 carbon atoms;
$X^5$ is —C(O)O—; and
$R^D$ is hydrogen or an alkyl group comprising 2 to 6 carbon atoms.

In an even more preferred embodiment, said one or more phosphate compounds of formula (III) is one or more (preferably both) of the following two compounds

[Chemical structures shown]

R = C$_2$-C$_5$ alkyl

The lower limit for the total amount of said phosphorus-containing anti-wear agent (which typically is one or more phosphate anti-wear agents) is 100 ppm, but preferably may be higher, e.g. 200 ppm, 300 ppm, 400 ppm, 500 ppm, 600 ppm, 700 ppm, 800 ppm, 900 ppm, 1000 ppm, 1100 ppm, 1200 ppm, 1300 ppm or 1400 ppm. The upper limit for the total amount of said phosphorus-containing anti-wear agent (which typically is one or more phosphate anti-wear agents) is 3000 ppm, but in some (low phosphorus) embodiments may be lower, e.g. 2900 ppm, 2800 ppm, 2700 ppm, 2600 ppm, 2500 ppm, 2400 ppm, 2300 ppm, 2200 ppm, 2100 ppm, 2000 ppm, 1900 ppm, 1800 ppm, 1700 ppm, 1600 ppm or 1500 ppm. Preferred concentration ranges are e.g. 500 to 2500 ppm, or 750 to 2000 ppm, or 900 to 1600 ppm.

The lower limit for the total amount of said phosphorus-containing anti-wear agent (which typically is one or more phosphate anti-wear agents) in terms of phosphorus content (based on the total weight of the hydraulic fluid) is typically 10 ppm, but preferably may be higher, e.g. 20 ppm, 30 ppm, 40 ppm, 50 ppm, 60 ppm, 70 ppm, 80 ppm, 90 ppm, 100 ppm, 110 ppm, 120 ppm or 130 ppm. The upper limit for the total amount of said phosphorus-containing anti-wear agent (which typically is one or more phosphate anti-wear agents) in terms of phosphorus content (based on the total weight of the hydraulic fluid) is typically 300 ppm, but in some (low phosphorus) embodiments may be lower, e.g. 290 ppm, 280 ppm, 270 ppm, 260 ppm, 250 ppm, 240 ppm, 230 ppm, 220 ppm, 210 ppm, 200 ppm, 190 ppm or 180 ppm. Preferred concentration ranges are e.g. 50 to 250 ppm, or 75 to 200 ppm, or 100 to 160 ppm.

In a particularly preferred embodiment, said phosphorus-containing anti-wear agent (which typically is one or more phosphate anti-wear agents) is a combination of (i) a compound of formula (III) or a tribologically acceptable salt thereof, wherein each $R^A$ and $R^B$ is independently an alkyl group comprising 2 to 6 carbon atoms (typically 4 carbon atoms, such as isobutyl); $X^1$ and $X^4$ are S; $X^2$ and $X^3$ are O; $R^C$ is a divalent alkyl group comprising 2 to 6 carbon atoms (typically —$CH_2$—$CH(CH_3)$—); $X^5$ is —C(O)O—; and $R^D$ is hydrogen; and (ii) a compound of formula (II) or a tribologically acceptable salt thereof, wherein each $R^A$ and $R^B$ is independently an alkyl group comprising 2 to 6 carbon atoms (typically 3 carbon atoms, such as isopropyl); $X^1$ and $X^4$ are S; $X^2$ and $X^3$ are O; $R^C$ is a divalent alkyl group comprising 2 to 6 carbon atoms (typically ethylene); $X^5$ is —C(O)O—; and $R^D$ is an alkyl group comprising 2 to 6 carbon atoms. In this regard, it is preferred that agent (i) is used in an amount of 100 to 2000 ppm, preferably 200 to 1500 ppm, more preferably 250 to 1200 ppm, and/or (preferably and) that agent (ii) is used in an amount of 400 to 2800 ppm, preferably 600 to 2500 ppm, more preferably 750 to 2000 ppm, more preferably still 750 to 1500 ppm.

Preferably the hydraulic fluid is substantially free of anti-wear agents other than the above described phosphorus-containing anti-wear agent.

Preferably the hydraulic fluid is substantially free of phosphorous-containing compounds other than the above described phosphorus-containing anti-wear agent.

Preferably the hydraulic fluid is substantially free of anti-wear agents and phosphorous-containing compounds other than the above described phosphorus-containing anti-wear agent.

For instance, in preferred aspects of the invention wherein the above described phosphorus-containing anti-wear agent is a particular subset/type of phosphate anti-wear agent or a combination thereof, the hydraulic fluid is preferably substantially free of any other phosphate anti-wear agent.

Preferably the total content of phosphorus containing compounds (of any kind) in the hydraulic fluid is 100 to 3000 ppm by weight. More preferably, the total content of phosphorus containing compounds is at most 2600 ppm, such as at most 2400 ppm, at most 2200 ppm, at most 2100 ppm, or at most 2000 ppm. Typically the total content of phosphorus containing compounds (when present) corresponds essentially to the concentration of the above phosphorus-containing anti-wear agent.

Preferably the total phosphorus content of the hydraulic fluid is at most 2000 ppm, such as at most 1000 ppm, at most 800 ppm, at most 500 ppm, at most 400 ppm or at most 300 ppm. The present invention also enables the formulation of low phosphorus content fluids. Thus, in a further preferred embodiment the total phosphorus content of the hydraulic fluid is at most 250 ppm, at most 220 ppm, at most 200 ppm or at most 180 ppm. Typically the total phosphorus content of the hydraulic fluid is at least 20 ppm, such as at least 40 ppm, at least 60 ppm, at least 80 ppm, at least 100 ppm or at least 120 ppm. In particular preferred aspects the total phosphorus content of the hydraulic fluid is 50 to 500 ppm, 100 to 300 ppm, or 120 to 180 ppm. Phosphorus content may preferably be measured by ASTM D4951.

As mentioned above the phosphorus-containing anti-wear agent is preferably ashless. Moreover, preferably the total zinc content of the hydraulic fluid is at most 500 ppm, more preferably at most 400 ppm, more preferably still at most 300 ppm, such as at most 200 ppm, at most 100 ppm, at most 50 ppm, at most 20 ppm or at most 10 ppm. In a particularly preferred embodiment the hydraulic fluid is essentially free of zinc. Zinc content may preferably be measured by ASTM D4951.

Optional Rust Inhibitor Component

The hydraulic fluid of the present invention preferably further comprises one or more rust inhibitors. Preferably said one or more rust inhibitors comprise at least one sulfonate rust inhibitor, and more preferably at least one derivative of an optionally substituted naphthalenesulfonic acid, which derivative is selected from the group consisting of:

(i) neutral metal salts of a naphthalenesulfonic acid,
(ii) basic metal salts of a naphthalenesulfonic acid,
(iii) metal complexes of amine salts of a naphthalenesulfonic acid, and
(iv) esters of a naphthalenesulfonic acid, wherein the naphthalenesulfonic acid is preferably a compound of the following formula:

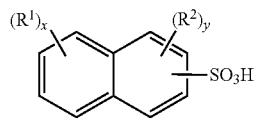

wherein each $R^1$ and each $R^2$ is independently a hydrocarbyl group comprising 1 to 30 carbon atoms, x is 0 to 4, and y is 0 to 3. Preferably x+y≥1. Preferably the hydrocarbyl groups are alkyl groups. Thus, preferably the optionally substituted naphthalenesulfonic acid is a mono-, di, or poly-alkylated naphthalenesulfonic acid. Suitable derivatives are described in U.S. Pat. No. 6,436,882. Such agents can be particularly useful in enhancing the corrosion inhibiting properties of the fluids of the invention. Preferably in this regard, said hydrocarbyl group has at least 4 carbon atoms, more preferably at least 10 carbon atoms. Preferably said hydrocarbyl group has up to 20 carbon atoms, more preferably up to 14 carbon atoms. Preferably said hydrocarbyl group is a straight or branched alkyl group, more preferably a straight alkyl group.

Preferably the derivative is a Ca alkylnaphthalenesulfonate/carboxylate complex. The Ca content of the complex is preferably 1.5 to 3.0% by weight, such as 2.0 to 2.5% by weight. Typically it is around 2.2% by weight.

The lower limit for the total amount of said one or more rust inhibitors, when present, is preferably 10 ppm, but more preferably is higher, e.g. 20 ppm, 40 ppm, 60 ppm, 80 ppm or 100 ppm. The upper limit for the total amount is preferably 2000 ppm, but more preferably may be lower, e.g. 1800 ppm, 1700 ppm, 1600 ppm, 1500 ppm, 1400 ppm, 1300 ppm, 1200 ppm, 1100 ppm, 1000 ppm or 900 ppm. Typical preferred concentration ranges are e.g. 40 to 1500 ppm, or 100 to 1000 ppm.

Optional Antioxidant Components

The hydraulic fluid of the present invention preferably further comprises one or more antioxidants.

In this regard, the term "one or more antioxidants" preferably means one, two, or three antioxidant(s), more preferably one or two antioxidant(s), and most preferably two antioxidants. For the avoidance of doubt, though, in situations where the term "one or more" is defined as a particular number, e.g. two, this does not preclude the presence of further antioxidants.

Preferably said one or more antioxidants are selected from phenolic antioxidants (typically hindered phenol antioxidants) and/or amine antioxidants (typically aromatic amine antioxidants). In a particularly preferred embodiment, said one or more antioxidants is a phenolic antioxidant and an amine antioxidant.

Preferred phenolic antioxidants are alkylated monophenols. Examples of alkylated monophenol antioxidants include 2,6-di-tert-butyl-phenol, 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, and combinations thereof.

Examples of amine antioxidants include N,N'-dinonyl-p-phenylenediamine, N,N'-dioctyl-p-phenylenediamine, N,N'-didecyl-p-phenylenediamine, N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenyl amine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine—for example p,p'-di-tert-octyldiphenylamine, 4-N-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethyl amino methylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetraphenyl-1,4-diaminobut-2-ene, and combinations thereof.

Preferred amine antioxidants are aromatic amine antioxidants, and in particular dialkylated or diarylated diarylamine antioxidants, such as dialkylated/diarylated diphenyl amine antioxidants. Thus, preferably the amine antioxidant is N,N'-dialkyl-p-phenylenediamine or N,N'-diaryl-p-phenylenediamine. More preferably in this regard the aryl moieties are unsubstituted or substituted phenyl and the alkyl moieties contain 1 to 20 carbon atoms, such as 4 to 15 carbon atoms, or 7 to 12 carbon atoms. More preferably still, the amine antioxidant is an N,N'-dialkyl-p-phenylenediamine wherein the alkyl moieties contain 1 to 20 carbon atoms, such as 4 to 15 carbon atoms, or 7 to 12 carbon atoms.

The total amount of said one or more antioxidants (preferably a phenolic antioxidant and an amine antioxidant), when present, is preferably from 500 ppm to 5000 ppm. The lower limit may preferably be e.g. 600 ppm, 700 ppm, 800 ppm, 900 ppm, 1000 ppm, 1100 ppm or 1200 ppm. The upper limit may preferably be e.g. 4500 ppm, 4000 ppm, 3500 ppm, 3200 ppm, 3000 ppm, 2900 ppm, 2800 ppm, 2700 ppm or 2600 ppm. Typical preferred concentration ranges are e.g. 1000 to 3500 ppm, or 1500 to 2600 ppm.

In a particularly preferred embodiment, said one or more antioxidants is a phenolic antioxidant and an amine antioxidant, wherein the phenolic antioxidant is an alkylated monophenol (preferably 2,6-di-tert-butyl-phenol) and the amine antioxidant is an N,N'-dialkyl-p-phenylenediamine wherein the alkyl moieties contain 7 to 12 carbon atoms (preferably N,N'-dinonyl-p-phenylenediamine).

In preferred aspects wherein said one or more antioxidants is a phenolic antioxidant and an amine antioxidant, the amount of the phenolic antioxidant is preferably from 400 to 4000 ppm, and the amount of the amine antioxidant is preferably from 100 to 1000 ppm. The lower limit for the amount of the phenolic antioxidant is preferably 500 ppm, 600 ppm, 700 ppm, 800 ppm, 900 ppm, or 1000 ppm. In some cases it may be higher still, such as 1200 ppm or 1500 ppm. The upper limit for the amount of the phenolic antioxidant is preferably 3500 ppm, 3000 ppm, 2500 ppm, 2300 ppm, 2200 ppm, 2100 ppm or 2000 ppm. The lower limit for the amount of the amine antioxidant is preferably 150 ppm, 180 ppm, 200 ppm, 220 ppm, 240 ppm or 250 ppm. In some cases it may be higher still, such as 280 ppm, 300 ppm, or 320 ppm. The upper limit for the amount of the amine antioxidant is preferably 700 ppm, such as 600 ppm, 550 ppm, 500 ppm. In some cases it may be lower still, such as 450 ppm, 400 ppm, or 380 ppm.

Base Oil

The hydraulic fluid of the present invention comprises a major amount of a base oil. The term "major amount" means that the base oil accounts for the majority of the hydraulic fluid in terms of weight, i.e. it accounts for at least 50% by weight. Typically the base oil accounts for at least 60%, such as at least 70%, at least 80%, at least 85%, at least 90%, at least 92%, or at least 93%. The base oil may account for the vast majority of the hydraulic fluid, such as up to 99.6%, up to 99.5%, up to 99.4%, up to 99.3% or up to 99.2%. Typically the base oil accounts for 90.0 to 99.6%, such as 92.0 to 99.6% or 93.0 to 99.2% by weight of the hydraulic fluid.

The base oil may be a natural oil, a synthetic oil, or mixture of one or more natural oils and/or one or more synthetic oils.

The base oil, particularly when it is a mineral oil, may have a kinematic viscosity of 2.0 mm$^2$/s (cSt) to 25.0 mm$^2$/s (cSt) at 100° C. The hydraulic fluid may though also comprise certain amounts of oils with other viscosities, e.g. oils derived from the carrier fluids used to deliver some of the additives. Thus, the hydraulic fluid may comprise delivering fluids with kinematic viscosity between 32 and 68.

Suitable natural oils are an animal oil, a vegetable oil (e.g., castor oil and lard oil), a petroleum oil, a mineral oil, or an oil derived from coal or shale. Preferably the natural oil is mineral oil.

In a preferred embodiment the base oil is a mineral oil. Suitable mineral oils include all common mineral oil basestocks.

The mineral oil preferably has a sulfur content of no more than 2000 ppm, preferably no more than 1500 ppm, and more preferably no more than 1200 ppm. In some embodiments the sulfur content may be lower still, such no more than 300 ppm, no more than 100 ppm, no more than 50 ppm, no more than 20 ppm, or no more than 10 ppm.

The mineral oil preferably has a saturates content of at least 90%, more preferably at least 95%, at least 97%, or at least 98%.

The mineral oil is preferably a Group I, Group II or Group III base oil, or a mixture of two or more base oils selected from Group I, Group II and Group III base oils.

The mineral oil may be naphthenic or paraffinic. The mineral oil may be refined by conventional methodology using acid, alkali, and clay or other agents such as aluminum chloride, or may be an extracted oil produced, e.g. by solvent extraction with solvents such as phenol, sulfur dioxide, furfural or dichlorodiethyl ether. The mineral oil may be hydrotreated or hydrofined, dewaxed by chilling or catalytic dewaxing processes, or hydrocracked, such as the Yubase® family of hydrockracked base oils from SK Innovation Co., Ltd. (Seoul, Korea). The mineral oil may be produced from natural crude sources or be composed of isomerized wax materials or residues of other refining processes.

Possible options for the synthetic oil include hydrocarbon oils and halo-substituted hydrocarbon oils such as oligomerized, polymerized, and interpolymerized olefins (e.g. polybutylenes, polypropylenes, propylene, isobutylene copolymers, chlorinated polylactenes, poly(1-hexenes), poly(1-octenes), poly-(1-decenes), and mixtures thereof); alkylbenzenes (e.g. dodecyl-benzenes, tetradecylbenzenes, dinonyl-benzenes, and di(2-ethylhexyl)benzene); polyphenyls (e.g. biphenyls, terphenyls, and alkylated polyphenyls); alkylated diphenyl ethers; and alkylated diphenyl sulfides. Preferred synthetic oils are oligomers of α-olefins, particularly oligomers of 1-decene.

Other possible options for the synthetic oil include alkylene oxide polymers, interpolymers, copolymers, and derivatives thereof where the terminal hydroxyl groups have been modified by e.g. esterification or etherification. Examples include: polyoxyalkylene polymers prepared by polymerization of ethylene oxide or propylene oxide; the alkyl and aryl ethers of these polyoxyalkylene polymers (e.g., methyl-polyisopropylene glycol ether having an average molecular weight of e.g. around 1000, and diphenyl ether of polypropylene glycol having a molecular weight of e.g. 1000-1500); and mono- and poly-carboxylic esters thereof (e.g. the acetic acid esters, mixed $C_3$-$C_8$ fatty acid esters, and the $C_{12}$ oxo-acid diester of tetraethylene glycol).

Other possible options for the synthetic oil include the esters of dicarboxylic acids (e.g. phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, or alkenyl malonic acids) with a variety of alcohols (e.g. butyl alcohol, hexyl alcohol, dodecyl alcohol, 2-ethylhexyl alcohol, ethylene glycol, diethylene glycol monoethers, or propylene glycol). Examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebasic acid with two moles of tetraethylene glycol and two moles of 2-ethylhexanoic acid. Preferred in this class of synthetic oils are adipates of $C_4$ to $C_{12}$ alcohols.

Esters useful as synthetic base oils also include those made from $C_5$ to $C_{12}$ monocarboxylic acids and polyols and polyol ethers such as neopentyl glycol, trimethylolpropane pentaerythritol, dipentaerythritol, and tripentaerythritol.

Other possible options for the synthetic oil include silicon-based oils, such as the polyalkyl-, polyaryl-, polyalkoxy-, or polyaryloxy-siloxane oils and silicate oils. Examples include tetra-ethyl silicate, tetraisopropyl silicate, tetra-(2-ethylhexyl)silicate, tetra-(4-methyl-2-ethylhexyl) silicate, tetra-(p-tert-butylphenyl)silicate, hexa-(4-methyl-2-pentoxy)-disiloxane, poly(methyl)-siloxanes and poly(methylphenyl)siloxanes.

Other synthetic oils include liquid esters of phosphorus-containing acids (e.g., tricresyl phosphate, trioctyl phosphate, and diethyl ester of decylphosphonic acid), polymeric tetra-hydrofurans, and poly-α-olefins. Naturally, though, liquid esters of phosphorus-containing acids will not be an appropriate choice of base oil for the preferred embodiments of the invention noted above wherein the hydraulic fluid contains relatively low levels of phosphorus.

Oils may be unrefined, refined, re-refined, or may contain a mixture of unrefined/refined/re-refined oils. Unrefined oils are obtained directly from a natural source or a synthetic source (e.g., coal, shale, or tar sands bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to the unrefined oils except that refined oils have been treated in one or more purification steps to improve one or more properties. Suitable purification techniques include distillation, hydro treating, dewaxing, solvent extraction, acid or base extraction, filtration, and percolation, all of which are known to those skilled in the art. Re-refined oils are obtained by treating used oils in processes similar to those used to obtain the refined oils. These re-refined oils are also known as reclaimed or reprocessed oils and are often additionally processed to remove spent additives and oil breakdown products. Base oils for use in the present invention are preferably refined or re-refined oils, and more preferably they are refined oils.

Other possible options for the base oil include oils derived from natural gas by a process such as the Fischer-Tropsch reaction, sometimes referred to as Gas-to-Liquid (GTL) basestocks.

In embodiments where the base oil is a mixture of one or more natural oils with one or more synthetic oils, the natural oil is preferably a mineral oil and/or (typically and) the synthetic oil is preferably an oil based on poly-α-olefins (PAO), for example oligomers of 1-decene.

Further Aspects of the Hydraulic Fluid

The hydraulic fluid of the present invention preferably comprises a demulsifier. Preferably the demulsifier is a non-ionic surfactant. More preferably it is a block copolymer terminating in hydroxyl groups.

The concentration of the demulsifier in the hydraulic fluid is preferably from 1 ppm to 500 ppm by weight. The amount is preferably at least 2 ppm, such as at least 5 ppm, at least 8 ppm, or at least 10 ppm. The upper limit for the amount is preferably 400 ppm, such as at most 300 ppm, at most 200 ppm, at most 150 ppm, at most 120 ppm or at most 100 ppm.

The hydraulic fluid of the present invention may comprise a viscosity modifier (VM), which may also be referred to as a viscosity index improver (VII). Examples of VIIs include polyacrylates, polymethacrylates, vinylpyrrolidone/methacrylate copolymers, polyvinylpyrrolidones, polybutenes, olefin copolymers, styrene/acrylate copolymers, polyethers, and combinations thereof. If present, the VII can be used in an amount to deliver a viscosity index (VI) of between 100 and 250. More preferably, the VII can be used in an amount to deliver a VI of between 145 and 190 for improved low temperature properties and/or system operating efficiency.

The hydraulic fluid of the present invention may have a kinematic viscosity of 15 mm$^2$/s (cSt) to 150 mm$^2$/s (cSt) at 100° C.

The hydraulic fluid of the present invention may comprise a pour point depressant (PPD). Examples of PPDs include polymethacrylate and alkylated naphthalene derivatives, and combinations thereof. If present, the PPD can be used in an amount of 0.001 to 1.0% by weight of the hydraulic fluid, for improved low temperature properties.

The hydraulic fluid of the present invention may comprise a carrier or solvent for (among others) the corrosion inhibiting agent. The corrosion inhibiting agent of the invention may be in solid form, in which case it is preferable to dissolve it in a carrier or solvent before contacting it with the other components of the hydraulic fluid. Thus, the hydraulic fluid of the present invention typically comprises 50 to 1000 ppm of a carrier or solvent that is suitable for dissolving the corrosion inhibiting agent (i.e. component (a)). The amount of the carrier (or solvent), if present, may be at least 100 ppm, such as at least 200 ppm or at least 300 ppm. The amount of the carrier (or solvent), if present, is preferably at most 800 ppm, such as at most 600 ppm, at most 500 ppm or at most 400 ppm. Preferably the carrier/solvent is an alcohol, typically an alkanol (i.e. a non-aromatic alcohol). Preferably the carrier/solvent is a primary alcohol. Preferred examples for the alcohol are straight or branched alkyl alcohols, having 4 to 10 carbon atoms. Suitable examples include 1-hexanol, 2-ethylhexanol, 1-octanol and 1-decanol.

Unless indicated otherwise (e.g. in relation to embodiments which introduce upper limits for the amount of certain types of compound), as a general rule the hydraulic fluid of the invention may optionally comprise one or more further additives that are known in the art, such as antioxidants (e.g. metal dithiophosphates and/or sulfurized olefins), which may be used in an amount of 0.2-1.5%; corrosion inhibitors (e.g. carboxylic acids, metal sulphonates and/or alkylated carboxylic acids), which may be used in an amount of 0.05-1.0%; defoamants (e.g. polysiloxanes and/or organic esters), which may be used in an amount of 0.5-50 ppm; anti-wear agents (e.g. aryl phosphates, zinc dialkyldithiophosphates and/or organic sulphur/phosphorus compounds), which may be used in an amount of 0.5-2.0%; viscosity index improvers (e.g. polymethacrylate esters, styrene isoprene copolymers and/or polyolefins), which may be used in an amount of 3-25%; pour point depressants (e.g. polymethacrylate esters and/or naphthalene wax condensation products), which may be used in an amount of 0.05-1.5%; friction modifiers (e.g. fatty acids and/or esters of fatty acids), which may be used in an amount of 0.1-1%; detergents (e.g. metal salicylates and/or metal sulphonates), which may be used in an amount of 0.02-0.2%; and/or (preferably and) seal swell agents (e.g. organic esters and/or aromatics), which may be used in an amount of 1-5%.

While the hydraulic fluid of the present invention may comprise various optional additives, it is preferred to avoid the unnecessary use of additives that will detract from the beneficial effects of the invention as described herein. Thus, it is preferred to avoid or minimise the use of additives which are harmful to seals and/or yellow metals (e.g. it is preferred to avoid the use of fatty imidazolines which can negatively affect seals). In line with this, it is preferred that the fluid may enjoy performance levels such as those noted below.

The hydraulic fluid of the present invention preferably provides passing scores, i.e. scores within the tolerance limits (more preferably within the ideal limits) in terms of one or more (preferably all) of the following properties determinable according to RFT-EC-Rexroth-Fluid-Test-Elastomer-Compatibility HLP/HVLP/HEPR: change in volume, change in weight, change in hardness, change in tensile strength and/or change in elongation at break. Preferably in this regard the seal used is an FKM fluoropolymer (or FKM fluoroelastomer) such as 75 FKM 595.

The hydraulic fluid of the present invention preferably scores a rating of at least 1B, and more preferably 1A, when tested according to the ASTM D130 Copper Strip Test, with the test being run for a time period of 3 hours and at a temperature of 100° C.

The hydraulic fluid of the present invention preferably scores a rating of at least 1B, and more preferably at least 1A, when tested according to the ASTM D130 Copper Strip Test, with the test being run for a time period of 3 hours and at a temperature of 121° C.

The hydraulic fluid of the present invention preferably provides (i) a copper weight loss of less than 0.15, more preferably less than 0.10; and/or (ii) a copper rating of at least 2B, more preferably at least 1B, when tested according to the ASTM D2619.

The hydraulic fluid of the present invention preferably provides a H2O TAN score of zero, when tested according to the ASTM D664.

The hydraulic fluid of the present invention preferably provides an RPVOT score of at least 300 minutes, more preferably at least 350 minutes, when tested according to the ASTM D2272 Standard Test Method for Oxidation Stability of Steam Turbine Oils by Rotating Pressure Vessel.

The hydraulic fluid of the present invention preferably achieves a pass in the ASTM D665 Standard Test Method for Rust-Preventing Characteristics of Inhibited Mineral Oil in the Presence of Water.

The hydraulic fluid of the present invention, when tested according to the ASTM D4310 Standard Test Method for Determination of Sludging and Corrosion Tendencies of Inhibited Mineral Oils, preferably achieves (i) a copper weight of 15 mg or less and preferably 13 mg or less; and/or (ii) an iron weight of 1.0 mg or less and preferably 0.7 mg or less.

Additive Concentrates

Lubricating oil compositions such as hydraulic fluids are routinely prepared by formulators by combining a base oil with an additive concentrate which contains multiple additives in a relatively high concentration. The present invention provides an additive concentrate comprising:

(a) 2.0 to 20% by weight of a corrosion inhibiting agent which is one or more compounds of formula (I):

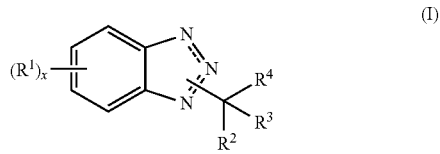

and/or tribologically acceptable salts thereof, wherein in formula (I):
each $R^1$ is independently a hydrocarbyl group comprising 1 to 10 carbon atoms,
x is 0 to 4,
each of $R^2$ and $R^3$ is independently hydrogen or a hydrocarbyl group comprising 1 to 20 carbon atoms;
$R^4$ is —$NR^5R^6$ or —$OR^7$,
each of $R^5$ and $R^6$ is independently an aryl group comprising 6 to 14 carbon atoms, optionally substituted with one or more hydrocarbyl groups comprising 1 to 20 carbon atoms,
$R^7$ is a hydrocarbyl group comprising 1 to 20 carbon atoms, and
in each of said hydrocarbyl groups containing 2 or more carbon atoms, the carbon chain may, independently, optionally be interrupted by one or more ether groups;

(b) 11 to 50% by weight (preferably 11 to 45% by weight) of an ashless nitrogen-containing dispersant; and optionally (c) a diluent.

Preferably the corrosion inhibiting agent is present in an amount of at least 2.3%, more preferably at least 2.6%, more preferably still at least 2.8%, and typically at least 3.0% by weight. The upper limit for the amount of the corrosion inhibiting agent is preferably 15%, more preferably 13%, more preferably still 11%, and typically 9.0% by weight. Typically the corrosion inhibiting agent is present in an amount of 2.3 to 15% by weight, more typically 3.0 to 9.0%.

When $R^4$ is —$NR^5R^6$, the corrosion inhibiting agent is preferably present in an amount of at least 2.3%, more preferably at least 2.6%, more preferably still at least 2.8%, and typically at least 3.0% by weight. When $R^4$ is —$NR^5R^6$ the upper limit for the amount of the corrosion inhibiting agent is preferably 18%, more preferably 16%, more preferably still 15%, and typically 14% by weight. When $R^4$ is —$NR^5R^6$ the corrosion inhibiting agent is typically present in an amount of 3.0 to 14% by weight.

When $R^4$ is —$OR^7$, the corrosion inhibiting agent is preferably present in an amount of at least 2.1%, more preferably at least 2.2%, and typically at least 2.3% by weight. When $R^4$ is —$OR^7$ the upper limit for the amount of the corrosion inhibiting agent is preferably 15%, more preferably 13%, more preferably still 11%, and typically 9.0% by weight. When $R^4$ is —$OR^7$ the corrosion inhibiting agent is typically present in an amount of 2.0 to 11%, more typically 2.0 to 9.0% by weight, a yet more typically 2.3 to 9.0% by weight.

Preferably the dispersant is present in an amount of at least 11%, more preferably at least 12%, and typically at least 13% by weight. The upper limit for the amount of the dispersant is preferably 48%, more preferably 46%, and typically 45% by weight. Typically the dispersant is present in an amount of 13 to 45% by weight.

Preferably the corrosion inhibiting agent is present in an amount of 2.3 to 15% by weight and the dispersant is present in an amount of 13 to 45% by weight.

Preferably the additive concentrate further comprises one or more metal detergents. Said one or more metal detergents are preferably present in an amount of at least 0.4%, more preferably at least 0.5%, more preferably still at least 0.6% and typically at least 0.7% by weight. The upper limit for the amount of said one or more metal detergents is preferably 15%, more preferably 12%, more preferably still 10%, and typically 8.0% by weight. Typically said one or more metal detergents are present in an amount of 0.7 to 8.0% by weight.

Preferably the additive concentrate further comprises a phosphorus-containing anti-wear agent. More preferably the phosphorus-containing anti-wear agent is one or more phosphate anti-wear agents. Said phosphorus-containing anti-wear agent (which preferably is one or more phosphate anti-wear agents) is preferably present in an amount of at least 0.7%, more preferably at least 3.7%, more preferably still at least 5.5% and typically at least 6.5% by weight. The upper limit for the amount of said phosphorus-containing anti-wear agent (which preferably is one or more phosphate anti-wear agents) is preferably 23%, more preferably 19%, more preferably still 15% by weight. Typically said phosphorus-containing anti-wear agent (which preferably is one or more phosphate anti-wear agents) is present in an amount of 6.5 to 15% by weight.

Preferably the additive concentrate further comprises one or more antioxidants. Said one or more antioxidants are preferably present in an amount of at least 3.7%, more preferably at least 7.5%, and typically at least 11% by weight. The upper limit for the amount of said one or more antioxidants is preferably 37%, more preferably 30%, and typically 26% by weight. Typically said one or more antioxidants are present in an amount of 11 to 26% by weight.

Preferably the additive concentrate further comprises one or more rust inhibitors. Said one or more rust inhibitors are preferably present in an amount of at least 0.07%, more preferably at least 0.3%, and typically at least 0.7% by weight. The upper limit for the amount of said one or more rust inhibitors is preferably 15%, more preferably 13%, and typically 11% by weight. Typically said one or more rust inhibitors are present in an amount of 0.7 to 11% by weight.

Preferably the additive concentrate further comprises a demulsifier. Said demulsifier is preferably present in an amount of at least 0.007%, more preferably at least 0.04%, and typically at least 0.07% by weight. The upper limit for the amount of said one or more demulsifier is preferably 3.7%, more preferably 2.3%, and typically 1.0% by weight. Typically said one or more demulsifiers are present in an amount of 0.07 to 1.0% by weight.

In a typical embodiment, the additive concentrate (further) comprises:

(i) one or more metal detergents in an amount of 0.7 to 8.0% by weight;

(ii) one or more phosphate anti-wear agents in an amount of 0.7 to 23% by weight;

(iii) one or more antioxidants in an amount of 3.7 to 37% by weight;

(iv) one or more rust inhibitors in an amount of 0.07 to 15% by weight; and/or (v) a demulsifier in an amount of 0.007 to 3.7% by weight.

The features set out above/herein relating to the nature of the additives that may be present in the hydraulic fluid of the invention (i.e. the corrosion inhibiting, dispersant, detergent, anti-wear, antioxidant, rust inhibitor, and demsulfier components) also apply (independently) to the additives for use in the additive concentrate of the invention.

The additive concentrate preferably comprises a diluent.

When a diluent is present, the identity of any substances making up the diluent is not particularly limited. Any substances which are suitable for serving as a carrier for one or more of the additive components present may be used. Typically the diluent is a base oil. The features set out above/herein relating to the nature of the base oil that is present in the hydraulic fluid of the invention also apply (independently) to the base oil for possible use as a diluent in the additive concentrate of the invention.

The additive concentrate of the invention is preferably suitable for use in preparing a hydraulic fluid of the present invention as defined herein (e.g. by combining an appropriate amount of the additive concentrate with a base oil).

A Compound of Formula (II) or a Tribologically Acceptable Salt Thereof

The present invention also provides a compound of formula (II):

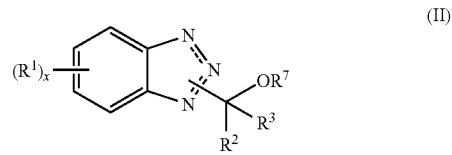

(II)

or a tribologically acceptable salt thereof, wherein in formula (II):
each $R^1$ is independently a hydrocarbyl group comprising 1 to 10 carbon atoms,
x is 0 to 4,
each of $R^2$ and $R^3$ is independently hydrogen or a hydrocarbyl group comprising 1 to 20 carbon atoms,
$R^7$ is a group comprising 1 to 20 carbon atoms, and
in each of said hydrocarbyl groups containing 2 or more carbon atoms, the carbon chain may, independently, optionally be interrupted by one or more ether groups, provided that either
(a) between them $R^2$ and $R^3$ have at least 7 carbon atoms and $R^7$ has at least 2 carbon atoms,
(b) between them $R^2$ and $R^3$ have at least 5 carbon atoms and $R^7$ has at least 2 carbon atoms and is not a cycloalkyl group,
(c) neither of $R^2$ and $R^3$ is H, and between them $R^2$ and $R^3$ have at least 3 carbon atoms,
(d) x is 1 to 4, $R^1$ has at least 2 carbon atoms, and either (i) $R^7$ has at least 2 carbon atoms, (ii) neither of $R^2$ and $R^3$ is H, or (iii) between them $R^2$ and $R^3$ have at least 3 carbon atoms, or
(e) x is 2 to 4.

Preferably in formula (II), each $R^1$ is independently a straight or branched alkyl group or an aryl group such as phenyl. More preferably each $R^1$ is independently a straight or branched alkyl group.

Preferably, each $R^1$ independently comprises 1 to 8 carbon atoms, more preferably 1 to 6 carbon atoms, and yet more preferably 1 to 4 carbon atoms. Preferred examples for $R^1$ are alkyl groups such as methyl, ethyl, n-propyl, i-propyl, n-butyl, i-butyl, and t-butyl. Methyl and ethyl are particularly preferred, and methyl most preferred.

The upper limit for the moiety x is preferably 3, more preferably 2. The lower limit for x is preferably 1. It is particularly preferred for x to be 0 or 1. Most preferably, x is 1.

$R^2$ is preferably hydrogen or a straight or branched alkyl group or an aryl group such as phenyl. More preferably $R^2$ is a straight or branched alkyl group.

When $R^2$ is a hydrocarbyl group containing 1 to 20 carbon atoms, $R^2$ preferably comprises 2 to 16 carbon atoms, more preferably 4 to 12 carbon atoms, and yet more preferably 6 to 10 carbon atoms. Preferred examples for $R^2$ in this regard are alkyl groups such as the straight and branched forms of hexyl, heptyl, octyl, nonyl and decyl, with n-octyl most preferred.

$R^3$ is preferably hydrogen or a straight or branched alkyl group or an aryl group such as phenyl. More preferably $R^3$ is hydrogen or a straight or branched alkyl group. Most preferably $R^3$ is hydrogen.

When $R^3$ is a hydrocarbyl group containing 1 to 20 carbon atoms, it preferably comprises 1 to 8 carbon atoms, more preferably 1 to 6 carbon atoms, and yet more preferably 1 to 4 carbon atoms. Preferred examples for $R^3$ in this regard are alkyl groups such as methyl, ethyl, n-propyl, i-propyl, n-butyl, i-butyl, and t-butyl, with methyl and ethyl being particularly preferred, and methyl most preferred.

Preferably, $R^7$ is a straight or branched alkyl group or an aryl group such as phenyl. More preferably $R^7$ is a straight or branched alkyl group.

Preferably, $R^7$ comprises 1 to 10 carbon atoms, more preferably 2 to 8 carbon atoms, and yet more preferably 3 to 6 carbon atoms. Preferred examples for $R^7$ are alkyl groups such as the straight and branched forms of propyl, butyl, pentyl and hexyl, with n-butyl most preferred.

In a particularly preferred embodiment, x is 0 or 1, $R^1$ is a straight or branched alkyl group comprising 1 to 4 carbon atoms such as methyl or ethyl (typically methyl), $R^1$ is a straight or branched alkyl group comprising 4 to 12 carbon atoms and preferably 6 to 10 carbon atoms (typically n-octyl), $R^3$ is hydrogen or a straight or branched alkyl group comprising 1 to 4 carbon atoms such as methyl or ethyl (typically $R^3$ is hydrogen), and $R^7$ is a straight or branched alkyl group comprising 2 to 8 carbon atoms and preferably 3 to 6 carbon atoms (typically n-butyl). More preferably in this regard, x is 1.

In particularly preferred embodiments, $R^1$, $R^2$, $R^3$, and $R^7$ are defined in accordance with one of the following numbered embodiments:

|    | $R^1$  | x | $R^2$      | $R^3$ | $R^7$  |
|----|--------|---|------------|-------|--------|
| 1  | methyl | 1 | octyl      | H     | butyl  |
| 2  | methyl | 1 | nonyl      | H     | butyl  |
| 3  | methyl | 1 | decyl      | H     | butyl  |
| 4  | methyl | 1 | undecyl    | H     | butyl  |
| 5  | methyl | 1 | dodecyl    | H     | butyl  |
| 6  | methyl | 1 | tridecyl   | H     | butyl  |
| 7  | methyl | 1 | tetradecyl | H     | butyl  |
| 8  | methyl | 1 | pentadecyl | H     | butyl  |
| 9  | methyl | 1 | hexadecyl  | H     | butyl  |
| 10 | methyl | 1 | heptyl     | H     | butyl  |
| 11 | methyl | 1 | hexyl      | H     | butyl  |
| 12 | methyl | 1 | pentyl     | H     | butyl  |
| 13 | methyl | 1 | octyl      | H     | propyl |
| 14 | methyl | 1 | nonyl      | H     | propyl |
| 15 | methyl | 1 | decyl      | H     | propyl |
| 16 | methyl | 1 | undecyl    | H     | propyl |
| 17 | methyl | 1 | dodecyl    | H     | propyl |
| 18 | methyl | 1 | tridecyl   | H     | propyl |
| 19 | methyl | 1 | tetradecyl | H     | propyl |
| 20 | methyl | 1 | pentadecyl | H     | propyl |
| 21 | methyl | 1 | hexadecyl  | H     | propyl |
| 22 | methyl | 1 | heptyl     | H     | propyl |
| 23 | methyl | 1 | hexyl      | H     | propyl |
| 24 | methyl | 1 | pentyl     | H     | propyl |
| 25 | methyl | 1 | octyl      | H     | ethyl  |
| 26 | methyl | 1 | nonyl      | H     | ethyl  |
| 27 | methyl | 1 | decyl      | H     | ethyl  |
| 28 | methyl | 1 | undecyl    | H     | ethyl  |
| 29 | methyl | 1 | dodecyl    | H     | ethyl  |
| 30 | methyl | 1 | tridecyl   | H     | ethyl  |
| 31 | methyl | 1 | tetradecyl | H     | ethyl  |
| 32 | methyl | 1 | pentadecyl | H     | ethyl  |
| 33 | methyl | 1 | hexadecyl  | H     | ethyl  |
| 34 | methyl | 1 | heptyl     | H     | ethyl  |
| 35 | methyl | 1 | hexyl      | H     | ethyl  |
| 36 | methyl | 1 | pentyl     | H     | ethyl  |
| 37 | methyl | 1 | octyl      | H     | pentyl |
| 38 | methyl | 1 | nonyl      | H     | pentyl |
| 39 | methyl | 1 | decyl      | H     | pentyl |
| 40 | methyl | 1 | undecyl    | H     | pentyl |
| 41 | methyl | 1 | dodecyl    | H     | pentyl |
| 42 | methyl | 1 | tridecyl   | H     | pentyl |
| 43 | methyl | 1 | tetradecyl | H     | pentyl |
| 44 | methyl | 1 | pentadecyl | H     | pentyl |
| 45 | methyl | 1 | hexadecyl  | H     | pentyl |
| 46 | methyl | 1 | heptyl     | H     | pentyl |
| 47 | methyl | 1 | hexyl      | H     | pentyl |
| 48 | methyl | 1 | pentyl     | H     | pentyl |
| 49 | methyl | 1 | octyl      | H     | hexyl  |
| 50 | methyl | 1 | nonyl      | H     | hexyl  |
| 51 | methyl | 1 | decyl      | H     | hexyl  |
| 52 | methyl | 1 | undecyl    | H     | hexyl  |
| 53 | methyl | 1 | dodecyl    | H     | hexyl  |
| 54 | methyl | 1 | tridecyl   | H     | hexyl  |
| 55 | methyl | 1 | tetradecyl | H     | hexyl  |
| 56 | methyl | 1 | pentadecyl | H     | hexyl  |
| 57 | methyl | 1 | hexadecyl  | H     | hexyl  |
| 58 | methyl | 1 | heptyl     | H     | hexyl  |
| 59 | methyl | 1 | hexyl      | H     | hexyl  |
| 60 | methyl | 1 | pentyl     | H     | hexyl  |

-continued

| | R¹ | x | R² | R³ | R⁷ |
|---|---|---|---|---|---|
| 61 | methyl | 1 | octyl | H | heptyl |
| 62 | methyl | 1 | nonyl | H | heptyl |
| 63 | methyl | 1 | decyl | H | heptyl |
| 64 | methyl | 1 | undecyl | H | heptyl |
| 65 | methyl | 1 | dodecyl | H | heptyl |
| 66 | methyl | 1 | tridecyl | H | heptyl |
| 67 | methyl | 1 | tetradecyl | H | heptyl |
| 68 | methyl | 1 | pentadecyl | H | heptyl |
| 69 | methyl | 1 | hexadecyl | H | heptyl |
| 70 | methyl | 1 | heptyl | H | heptyl |
| 71 | methyl | 1 | hexyl | H | heptyl |
| 72 | methyl | 1 | pentyl | H | heptyl |
| 73 | methyl | 1 | octyl | H | octyl |
| 74 | methyl | 1 | nonyl | H | octyl |
| 75 | methyl | 1 | decyl | H | octyl |
| 76 | methyl | 1 | undecyl | H | octyl |
| 77 | methyl | 1 | dodecyl | H | octyl |
| 78 | methyl | 1 | tridecyl | H | octyl |
| 79 | methyl | 1 | tetradecyl | H | octyl |
| 80 | methyl | 1 | pentadecyl | H | octyl |
| 81 | methyl | 1 | hexadecyl | H | octyl |
| 82 | methyl | 1 | heptyl | H | octyl |
| 83 | methyl | 1 | hexyl | H | octyl |
| 84 | methyl | 1 | pentyl | H | octyl |
| 85 | — | 0 | octyl | H | butyl |
| 86 | — | 0 | nonyl | H | butyl |
| 87 | — | 0 | decyl | H | butyl |
| 88 | — | 0 | undecyl | H | butyl |
| 89 | — | 0 | dodecyl | H | butyl |
| 90 | — | 0 | tridecyl | H | butyl |
| 91 | — | 0 | tetradecyl | H | butyl |
| 92 | — | 0 | pentadecyl | H | butyl |
| 93 | — | 0 | hexadecyl | H | butyl |
| 94 | — | 0 | heptyl | H | butyl |
| 95 | — | 0 | hexyl | H | butyl |
| 96 | — | 0 | pentyl | H | butyl |
| 97 | — | 0 | octyl | H | propyl |
| 98 | — | 0 | nonyl | H | propyl |
| 99 | — | 0 | decyl | H | propyl |
| 100 | — | 0 | undecyl | H | propyl |
| 101 | — | 0 | dodecyl | H | propyl |
| 102 | — | 0 | tridecyl | H | propyl |
| 103 | — | 0 | tetradecyl | H | propyl |
| 104 | — | 0 | pentadecyl | H | propyl |
| 105 | — | 0 | hexadecyl | H | propyl |
| 106 | — | 0 | heptyl | H | propyl |
| 107 | — | 0 | hexyl | H | propyl |
| 108 | — | 0 | pentyl | H | propyl |
| 109 | — | 0 | octyl | H | ethyl |
| 110 | — | 0 | nonyl | H | ethyl |
| 111 | — | 0 | decyl | H | ethyl |
| 112 | — | 0 | undecyl | H | ethyl |
| 113 | — | 0 | dodecyl | H | ethyl |
| 114 | — | 0 | tridecyl | H | ethyl |
| 115 | — | 0 | tetradecyl | H | ethyl |
| 116 | — | 0 | pentadecyl | H | ethyl |
| 117 | — | 0 | hexadecyl | H | ethyl |
| 118 | — | 0 | heptyl | H | ethyl |
| 119 | — | 0 | hexyl | H | ethyl |
| 120 | — | 0 | pentyl | H | ethyl |
| 121 | — | 0 | octyl | H | pentyl |
| 122 | — | 0 | nonyl | H | pentyl |
| 123 | — | 0 | decyl | H | pentyl |
| 124 | — | 0 | undecyl | H | pentyl |
| 125 | — | 0 | dodecyl | H | pentyl |
| 126 | — | 0 | tridecyl | H | pentyl |
| 127 | — | 0 | tetradecyl | H | pentyl |
| 128 | — | 0 | pentadecyl | H | pentyl |
| 129 | — | 0 | hexadecyl | H | pentyl |
| 130 | — | 0 | heptyl | H | pentyl |
| 131 | — | 0 | hexyl | H | pentyl |
| 132 | — | 0 | pentyl | H | pentyl |
| 133 | — | 0 | octyl | H | hexyl |
| 134 | — | 0 | nonyl | H | hexyl |
| 135 | — | 0 | decyl | H | hexyl |
| 136 | — | 0 | undecyl | H | hexyl |
| 137 | — | 0 | dodecyl | H | hexyl |
| 138 | — | 0 | tridecyl | H | hexyl |
| 139 | — | 0 | tetradecyl | H | hexyl |
| 140 | — | 0 | pentadecyl | H | hexyl |
| 141 | — | 0 | hexadecyl | H | hexyl |
| 142 | — | 0 | heptyl | H | hexyl |
| 143 | — | 0 | hexyl | H | hexyl |
| 144 | — | 0 | pentyl | H | hexyl |
| 145 | — | 0 | octyl | H | heptyl |
| 146 | — | 0 | nonyl | H | heptyl |
| 147 | — | 0 | decyl | H | heptyl |
| 148 | — | 0 | undecyl | H | heptyl |
| 149 | — | 0 | dodecyl | H | heptyl |
| 150 | — | 0 | tridecyl | H | heptyl |
| 151 | — | 0 | tetradecyl | H | heptyl |
| 152 | — | 0 | pentadecyl | H | heptyl |
| 153 | — | 0 | hexadecyl | H | heptyl |
| 154 | — | 0 | heptyl | H | heptyl |
| 155 | — | 0 | hexyl | H | heptyl |
| 156 | — | 0 | pentyl | H | heptyl |
| 157 | — | 0 | octyl | H | octyl |
| 158 | — | 0 | nonyl | H | octyl |
| 159 | — | 0 | decyl | H | octyl |
| 160 | — | 0 | undecyl | H | octyl |
| 161 | — | 0 | dodecyl | H | octyl |
| 162 | — | 0 | tridecyl | H | octyl |
| 163 | — | 0 | tetradecyl | H | octyl |
| 164 | — | 0 | pentadecyl | H | octyl |
| 165 | — | 0 | hexadecyl | H | octyl |
| 166 | — | 0 | heptyl | H | octyl |
| 167 | — | 0 | hexyl | H | octyl |
| 168 | — | 0 | pentyl | H | octyl |

An example of a preferred compound of formula (II) is Compound 1.

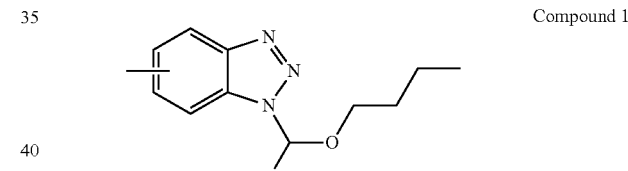

Compound 1

Compounds of formula (II) can be prepared by known methods, as is illustrated further below in the Examples section.

The present invention also provides a hydraulic fluid comprising a compound of formula (II) or tribologically acceptable salt thereof, wherein preferably the hydraulic fluid is as described herein.

Definitions

Unless indicated otherwise, all references herein to ppm or % are intended to refer to ppm or % in terms of weight. Also, unless indicated otherwise, all such references are intended to refer to the amount of the given substance relative to the total weight of the hydraulic fluid.

As used herein, the term "hydrocarbyl" refers to a group having a carbon atom directly attached to the rest of the molecule and having a hydrocarbyl or predominantly hydrocarbyl character. Non-hydrocarbon (hetero) atoms, groups or substituents may be present provided their presence does not alter the predominantly hydrocarbyl nature of the group—e.g. preferably there should be at least 4, more preferably at least 6, yet more preferably at least 8, and more preferably still at least 10 carbon atoms for every heteroatom, heteroatom-containing group or heteroatom-containing substituent (preferably for every heteroatom). Preferred heteroatoms are O, S, N and halo, and more preferred are O, S and N. Preferred heteroatom-containing groups or substituents are amine, keto, halo, hydroxy, nitro, cyano, alkoxy and acyl. Preferred are hydrocarbyl groups which contain at most one or two heteroatoms, heteroatom-containing groups or heteroatom-containing substituents. More preferred are hydrocarbyl groups based only on carbon and hydrogen atoms, and most preferred are aliphatic groups, in particular alkyl groups.

As used herein, the phrase "tribologically acceptable salt(s)", unless otherwise indicated, includes salts of acidic and/or basic groups. Thus, base addition salts and acid addition salts may be contemplated. As will be recognized by a skilled artisan, tribology is a term defining a study that deals with the interaction of surfaces in relative motion, in particular in terms of friction, lubrication and wear. Tribologically acceptable salts are salts that do not negate or interfere with the tribological activity of the compounds.

Bases that may be used to prepare base addition salts contemplated for compounds herein that are acidic in nature are those that form tribologically acceptable base addition salts with such compounds (i.e. salts containing tribologically acceptable cations). Such cations/base salts may include, but are not limited to, cations such as alkali metal cations (e.g. potassium and sodium) and alkaline earth metal cations (e.g. calcium and magnesium), ammonium or amine addition salts such as N-methylglucamine-(meglumine), and alkanolammonium and other base salts of tribologically acceptable organic amines, including but not limited to alkylamines such as octylamine and oleylamine, and also alkanolamines. In certain embodiments, however, the base addition salts of the compounds (in particular for compounds of formula (I)) are not amine salts. In this regard, it can also be preferred to minimize the content of amine salts generally in the hydraulic fluid of the invention. Thus, any other components (in particular antiwear agent(s)) present in the form of amine salts are preferably present in the hydraulic fluid of the invention in an amount less than or equal to about 1.0 wt %, less than or equal to about 0.5 wt %, less than or equal to about 0.1 wt %, less than or equal to about 0.05 wt %, less than or equal to about 0.01 wt %, or less than or equal to about 0.005 wt %.

Acids that may be used to prepare acid addition salts contemplated for compounds herein that are basic in nature are those that form tribologically acceptable acid addition salts with such compounds (i.e. salts containing tribologically acceptable anions). Such acid salts may include, but are not limited to, hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. Compounds of the present disclosure that include a basic moiety, such as an amino group, may form tribologically acceptable salts with various amines, in addition to the acids mentioned above.

Some of the compounds described herein and/or salts thereof may be able to exist in different tautomeric forms, as illustrated below for the compounds of formula (I). All such tautomeric forms are included within the scope of the present disclosure. In formula (I) this is reflected by the dotted lines between the adjacent nitrogen atoms in the triazole ring and the fact that the position of the —$CR^2R^3R^4$ group on this ring is left open. As a general rule, at any instances herein where just one tautomer may be described, alternative possible tautomeric forms are also envisaged.

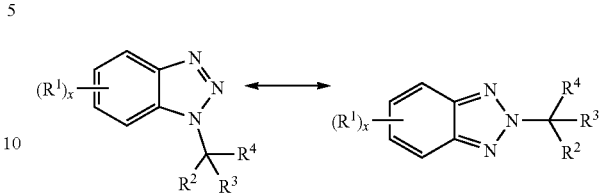

In instances where a compound described herein may exist in more than one different stereoisomeric form, all such stereoisomeric forms (e.g. optical isomers, i.e. R and S enantiomeric configurations), positional isomers, as well as racemic, diastereomeric and other mixtures of such isomers are envisaged and included within the scope of the present invention.

Hydraulic System of the Present Invention

The present invention provides a hydraulic system comprising at least one fluoropolymer seal and a hydraulic fluid of the present invention as defined herein which comes into contact with the seal.

The hydraulic system preferably also comprises one or more components comprising a yellow metal such as copper, brass or bronze, wherein said fluid comes into contact with the yellow metal. In particular, it is preferred for the hydraulic system to comprise one or more components comprising copper, wherein said fluid comes into contact with the copper. The yellow metal (typically copper) may be present, for instance, in one or more valves in the hydraulic system.

As used herein, the term fluoropolymer is intended to mean fluorine-containing elastomer, and may also be referred to as a fluoroelastomer. Preferably the fluoropolymer is one that is categorised as FKM, FFKM or FEPM according to ASTM D1418, and more preferably the fluoropolymer is one that is categorised as FKM according to ASTM D1418, i.e. more preferably the fluoropolymer is an FKM fluoropolymer (or FKM fluoroelastomer) such as 75 FKM 595.

In one embodiment the fluoropolymer is a copolymer of hexafluoropropylene (HFP) and vinylidene fluoride (VF2/VDF). In this regard, the fluoropolymer preferably has a fluorine content which (a) is at least 62 wt %, at least 64 wt %, or at least 65 wt %, and/or (b) is at most 72 wt %, at most 70 wt %, at most 68 wt %, or at most 67 wt %. Typically the fluorine content is around 66 wt %. Thus, the fluoropolymer may be a Type 1 FKM fluoropolymer. Type 1 FKM fluoropolymers may show good overall performance.

In another embodiment the fluoropolymer is a terpolymer of tetrafluoroethylene (TFE), hexafluoropropylene (HFP) and vinylidene fluoride (VF2/VDF). In this regard, the fluoropolymer preferably has a fluorine content which (a) is at least 62 wt %, at least 64 wt %, at least 66 wt %, or at least 67 wt %, and/or (b) is at most 74 wt %, at most 72 wt %, at most 71 wt %, or at most 70 wt %. Typically the fluorine content is around 68-69 weight %. Thus, the fluoropolymer may be a Type 2 FKM fluoropolymer. Type 2 FKM fluoropolymers may enable relatively good performance in terms of chemical and heat resistance, but a weaker compression set and low temperature flexibility.

In another embodiment the fluoropolymer is a terpolymer of tetrafluoroethylene (TFE), a fluorinated vinyl ether (PMVE), and vinylidene fluoride (VF2/VDF). In this regard, the fluoropolymer preferably has a fluorine content which (a) is at least 60 wt %, or at least 61 wt %, and/or (b) is at most 74 wt %, at most 72 wt %, at most 70 wt %, or at most 69 wt %. Typically the fluorine content is around 62-68 wt %. Thus, the fluoropolymer may be a Type 3 FKM fluoropolymer. Type 3 FKM fluoropolymers may provide relatively good performance in terms of low temperature flexibility.

In another embodiment the fluoropolymer is a terpolymer of tetrafluoroethylene (TFE), propylene (P) and vinylidene fluoride (VF2/VDF). In this regard, the fluoropolymer preferably has a fluorine content which (a) is at least 63 wt %, at least 65 wt %, or at least 66 wt %, and/or (b) is at most 73 wt %, at most 71 wt %, at most 69 wt %, or at most 68 wt %. Typically the fluorine content is around 67 wt %. Thus, the fluoropolymer may be a Type 4 FKM fluoropolymer. Type 4 FKM fluoropolymers may provide increased base resistance, but less desirable performance in terms of swelling properties, especially in hydrocarbons.

In another embodiment the fluoropolymer is a pentapolymer of tetrafluoroethylene (TFE), hexafluoropropylene (HFP), ethylene (E), a fluorinated vinyl ether (PMVE) and vinylidene fluoride (VF2/VDF). Thus, the fluoropolymer may be a Type 5 FKM fluoropolymer. Type 5 FKM fluoropolymers may enable good performance in terms of base resistance and high temperature hydrogen sulfide resistance.

In another embodiment the fluoropolymer is a perfluoroelastomer, wherein the polymer backbone is (substantially) fully fluorinated. In particular, the fluoropolymer may be a copolymer of tetrafluoroethylene (TFE) and perfluoromethylvinylether (MVE). (In this regard, the copolymer may also contain a unit derived from a cure-site monomer (CSM), i.e. a monomer that contains a site reactive towards free radicals—an example of such cure-site monomer is 4-bromo-3,3,4,4-tetrafluorobutene (BTFB)). Thus, all substituents on the polymer backbone in the perfluoroelastomer are preferably fluoro, perfluoroalkyl, or perfluoroalkoxy, and the fluoropolymer may be of the polymethacrylate type. In a particular aspect of this embodiment, the fluoropolymer may be an FFKM fluoropolymer.

In another embodiment the fluoropolymer is a copolymer of tetrafluoroethylene (TFE) and propylene (P). Thus, the fluoropolymer may be an FEPM fluoropolymer.

Preferred Aspects Relating to the Use of the Corrosion Inhibiting Agent

As explained above and demonstrated below in the Examples, the present invention is based on the finding that a certain type of corrosion inhibiting agent can provide robust corrosion inhibition at very low concentrations, particularly when combined with certain other additives, and that the benefits of this include improved fluoropolymer seal compatibility and improvements in the functional characteristics of fluoropolymer seal compatible fluids.

The present invention provides the use of 40 to 200 ppm by weight in terms of nitrogen content of a corrosion inhibiting agent as defined herein in a hydraulic fluid, to improve fluoropolymer seal compatibility.

The present invention provides the use of 40 to 200 ppm by weight in terms of nitrogen content of a corrosion inhibiting agent as defined herein in a hydraulic fluid, to preserve the integrity of one or more fluoropolymer seals which come into contact with said hydraulic fluid.

The present invention provides the use of 40 to 200 ppm by weight in terms of nitrogen content of a compound of formula (I) or a tribologically acceptable salt thereof in a hydraulic fluid, to inhibit corrosion while also improving fluoropolymer seal compatibility.

The present invention provides the use of 40 to 200 ppm by weight in terms of nitrogen content of a compound of formula (I) or a tribologically acceptable salt thereof in a hydraulic fluid, to inhibit corrosion while also preserving the integrity of one or more fluoropolymer seals which come into contact with said hydraulic fluid.

In the uses of the invention noted above, the hydraulic fluid is preferably as defined generally herein, i.e. the preferred aspects of the hydraulic fluid and the components thereof as set out above apply also to the uses of the invention noted above.

As will be readily apparent to the skilled person, references above to the improvement of fluoropolymer compatibility or the preservation of the integrity of one or more fluoropolymer seals refer to the fact that 40 to 200 ppm by weight in terms of nitrogen content of the specified agent degrades the fluoropolymer seal(s) at a lower rate than other corrosion inhibitors (such as Irgamet® 39) that might otherwise be employed at their usual treat rates.

Methods for determining such effects are known to the skilled person. For example, samples of the fluoropolymer material can be immersed in the hydraulic fluid comprising the specified component(s) for extended periods and at elevated temperatures, to mimic in-use conditions. The samples are then subjected to mechanical testing and/or physical measurement and compared to samples which have been exposed to one or more other fluid(s) and/or no fluid (as a control). A relevant technical effect may be an increase in tensile strength, an increase in elongation at break or a reduction in the change in volume, weight and/or hardness as compared to the other fluid(s).

Thus, in the context of the present invention, use to improve fluoropolymer seal compatibility or to preserve the integrity of a fluoropolymer seal, may preferably mean use (i) to reduce the rate of loss of the tensile strength of the fluoropolymer, (ii) to reduce the rate of decrease in elongation at break of the fluoropolymer, (iii) to reduce the rate of change in volume of the fluoropolymer, (iv) to reduce the rate of change in weight of the fluoropolymer, and/or (v) to reduce the rate of change in hardness of the fluoropolymer.

Fluoropolymer seal compatibility, and in particular any or all of the specific properties noted above (i.e. tensile strength, elongation at break, and change in volume, weight and/or hardness) may be determinable according to RFT-EC-Rexroth-Fluid-Test-Elastomer-Compatibility HLP/HVLP/HEPR: change in volume, change in weight, change in hardness, change in tensile strength and/or change in elongation at break. Preferably in this regard the seal is an FKM fluoropolymer (or FKM fluoroelastomer) such as 75 FKM 595.

In relation to the above uses of the invention, references to the inhibition of corrosion preferably refer to the corrosion of yellow metals, and more preferably copper.

For instance, references to the inhibition of corrosion may preferably refer to the inhibition of corrosion as determinable according to any of the standard tests discussed above, e.g. ASTM D130, ASTM D2619, ASTM D664, ASTM D2272, ASTM D4310 and/or ASTM D665.

Thus, references to the inhibition of corrosion may refer to the provision of any of the preferred performance characteristics for the hydraulic fluid of the invention (in terms of corrosion inhibition) that are noted above. For example, they may refer to the provision of (i) a rating of at least 1B and more preferably 1A, determinable according to ASTM D130 with the test being run for a time period of 3 hours at a temperature of 100° C., (ii) a rating of at least 1B and more preferably at least 1A, determinable according to ASTM D130 with the test being run for a time period of 3 hours at a temperature of 121° C.; (iii) a copper weight loss of less than 0.15, more preferably less than 0.10, determinable according to ASTM D2619; (iv) a copper rating of at least 2B, more preferably at least 1B, determinable according to ASTM D2619; (v) a H2O TAN score of zero, determinable according to ASTM D664; (vi) an RPVOT score of at least 300 minutes, more preferably at least 350, determinable according to ASTM D2272; (vii) a pass in the ASTM D665 test; and/or (viii) as determinable according to ASTM D4310, a copper weight of 15 mg or less and preferably 13 mg or less, and/or an iron weight of 1.0 mg or less and preferably 0.7 mg or less.

In relation to the above uses of the invention, references to the improvement of fluoropolymer seal compatibility or preservation of the integrity of a fluoropolymer seal preferably refer to one or more properties determinable according to RFT-EC-Rexroth-Fluid-Test-Elastomer-Compatibility HLP/HVLP/HEPR, such as one or more of the change in volume, change in weight, change in hardness, change in tensile strength and/or change in elongation at break. Preferably in this regard the seal used is an FKM fluoropolymer (or FKM fluoroelastomer) such as 75 FKM 595.

In preferred aspects, the present invention provides the use of a compound of formula (I) or a tribologically acceptable salt thereof, to inhibit corrosion in any one of the different respects noted above, while (also) degrading one or more fluoropolymer seals which come into contact with the fluid at a rate such that the hydraulic fluid provides passing scores, i.e. scores within the tolerance limits (more preferably within the ideal limits) in terms of one or more (preferably all) of the following properties determinable according to RFT-EC-Rexroth-Fluid-Test-Elastomer-Compatibility HLP/HVLP/HEPR: change in volume, change in weight, change in hardness, change in tensile strength and/or change in elongation at break. Preferably in this regard the seal used is an FKM fluoropolymer (or FKM fluoroelastomer) such as 75 FKM 595.

All of the above aspects of the hydraulic fluid and hydraulic system of the present invention described herein apply to the context of the above uses of the invention. Thus, in the context of the above uses, the hydraulic fluid is preferably a hydraulic fluid of the present invention as defined herein. Also, the hydraulic fluid and fluoropolymer seals are preferably comprised in a hydraulic system of the present invention as defined herein.

EXAMPLES

Some compounds of formula (I) are known and available commercially. In any case, the compounds may generally be prepared by known methods, such as by a Mannich reaction between (i) benzotriazole carrying one or more substituents on the benzene ring thereof (corresponding to the $R^1$ groups), (ii) $R^2C(=O)R^3$, and (iii) $R^4$—H which (depending on the identity of $R^4$) is an amine of formula $HNR^5R^6$ or an alcohol of formula $HOR^7$.

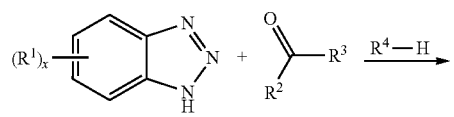

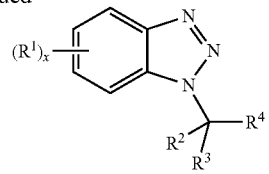

For instance, it is known that the preferred compound of formula (I) wherein $R^1$ is methyl, x is 1, $R^2$ and $R^3$ are hydrogen, $R^4$ is —$NR^5R^6$, and $R^5$ and $R^6$ are both 4-octylphenyl (i.e. the compound 1-[di(4-octylphenyl)aminomethyl]toluyltriazole) can be made by reacting toluyltriazole, formaldehyde and di(4-octylphenyl)amine (see e.g. U.S. Pat. No. 4,880,551), and the preferred compound of formula (I) wherein $R^1$ is methyl, x is 1, $R^2$ is hydrogen, $R^3$ is octyl, $R^4$ is $OR^7$, and $R^7$ is butyl can be prepared by reacting toluyltriazole, nonanal and butanol (see Example 1 below).

Example 1—Synthesis of Compound 1—1-[1-(butyloxy)octyl]toluyltriazole

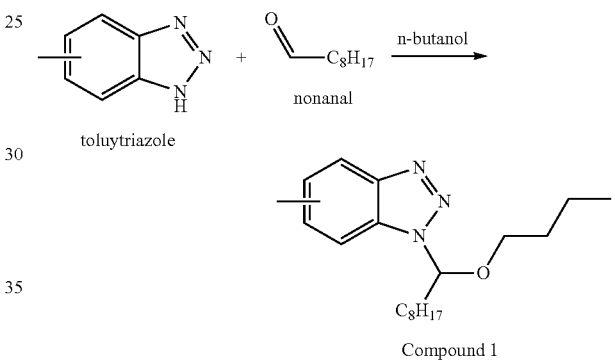

Figure 2:
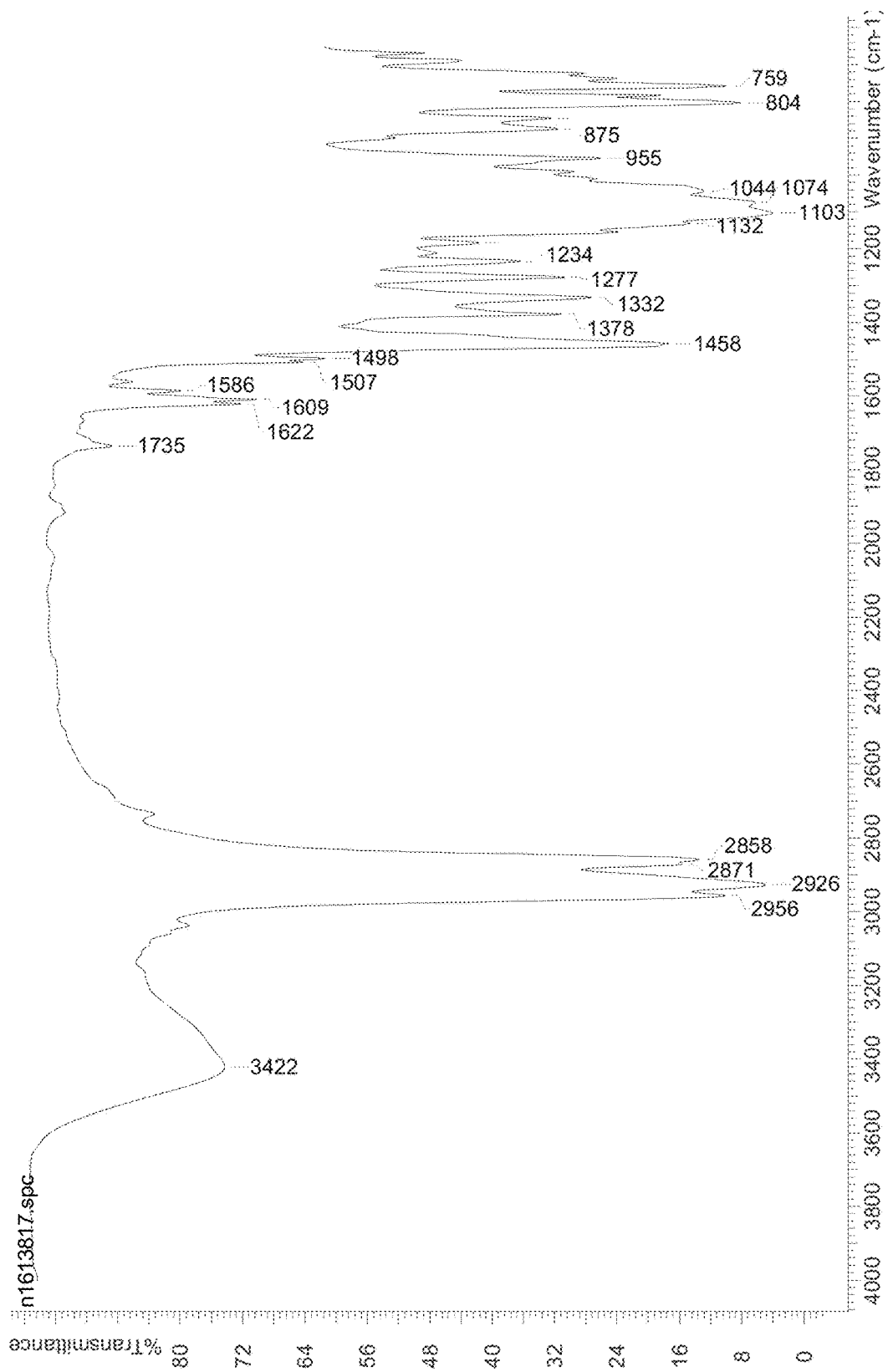
FIG. 2 is a FT-IR plot of the reaction product of Example 1.

To 44.3967 grams (0.33 moles) of toluyltriazole (mixture of isomers), 137 mLs (1.5 moles, excess) of n-butanol was added as both solvent and reagent. The toluyltriazole did not dissolve to any significant extent. To this reaction mixture, 46.94 grams (56.76 mLs, 0.33 moles) of nonanal was poured in one portion. An immediate exotherm was noted, from 19.6° C. to 31.6° C. Solution was heated to reflux and water was collected from azeotrope with n-butanol in Dean-Stark trap (5.94 mLs theoretical, actual not recorded). Excess n-butanol was removed by rotary evaporation followed by full pump vacuum. Crude yield was 122.8 g. % N Found 11.4, Calc. 12.8. The reaction product was then characterized by GC-MS (Table 1, FIG. 1) and FT-IR (FIG. 2).

TABLE 1

| GC-MS results for reaction product | | | | |
|---|---|---|---|---|
| Peak | RT | Area | Area Sum % | ID |
| 1 | 8.313 | 481649.74 | 2.4 | Alkoxy repeat |
| 2 | 9.456 | 470119.09 | 2.34 | Alkoxy repeat |
| 3 | 10.767 | 3501560.66 | 17.42 | C4/C9 ether |
| 4 | 13.534 | 502805.52 | 2.5 | Product |
| 5 | 13.788 | 658563.84 | 3.28 | Product |
| 6 | 14.036 | 5334332.25 | 26.54 | Product |
| 7 | 14.129 | 5329249.09 | 26.51 | Product |
| 8 | 14.256 | 3823162.63 | 19.02 | Product |

Example 2—Fluoropolymer Seal Compatibility Testing of Compound 1 vs Irgamet®

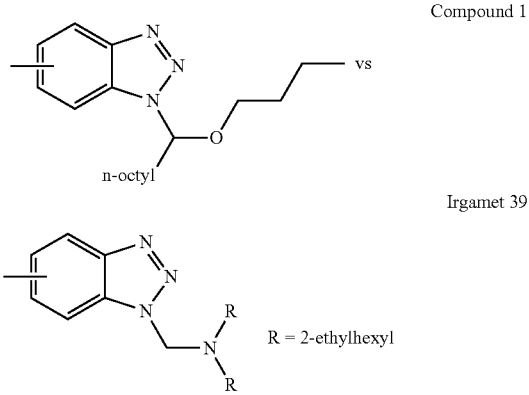

Compound 1 (1-[1-(butyloxy)octyl]toluyltriazole) and Irgamet 39 (which contains the above depicted compound without any diluent) were compared in the absence of other additives.

Thus, a first sample solution of single component system Compound 1 (0.189 wt %) in base oil was prepared, and then a second solution was also then prepared which differed from the first solution only in that it contained Irgamet® 39 (0.20 wt %) instead of Compound 1 (the use of relatively high concentrations of each of the additives meant that their negative impact on the seals was exaggerated, which allowed their respective effects to be more clearly distinguished from each other). Each solution was subjected to fluoropolymer seal compatibility testing performed against SAE J2643 FKM-1, which is bisphenol AF cured type II elastomer (samples of FKM fluoropolymer material were immersed in the solutions for a defined period of time and at a specific temperature). The seals from each sample were then analysed and their properties compared. In particular, the change in hardness, elongation and tensile stress of the samples were measured after 3, 7 and 14 days. Fluoropolymer seal compatibility test results are set out below in Table 2.

TABLE 2

FKM seal compatibility results for equimolar solutions of single component systems, Irgamet ® 39 and Compound 1, in base oil at 3, 7, and 14 days

| Sample | ΔHardness | ΔElongation (%) | ΔTensile Stress (%) |
|---|---|---|---|
| Irgamet ® 39 - 3 day | 3.50 | −47.85 | −46.42 |
| Irgamet ® 39 - 7 day | 5.40 | −71.18 | −66.89 |
| Irgamet ® 39 - 14 day | 4.70 | −78.20 | −71.78 |
| Compound 1-3 day | 0.70 | −0.73 | −11.80 |
| Compound 1-7 day | 0.50 | −5.44 | −11.82 |
| Compound 1-14 day | 1.60 | −16.96 | −13.93 |

Figure 3A:
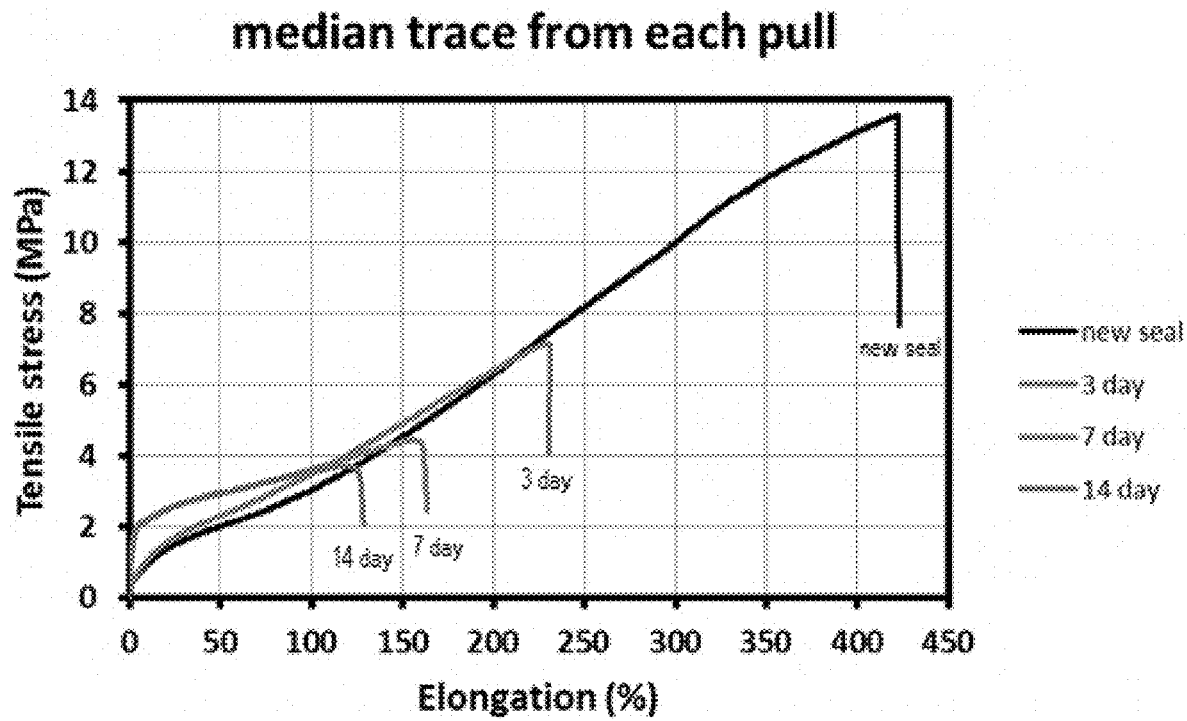
FIGS. 3a and 3b are tensile stress plots of solutions including Irgamet 39 and Compound 1, respectively, from Example 2.
Figure 3B:
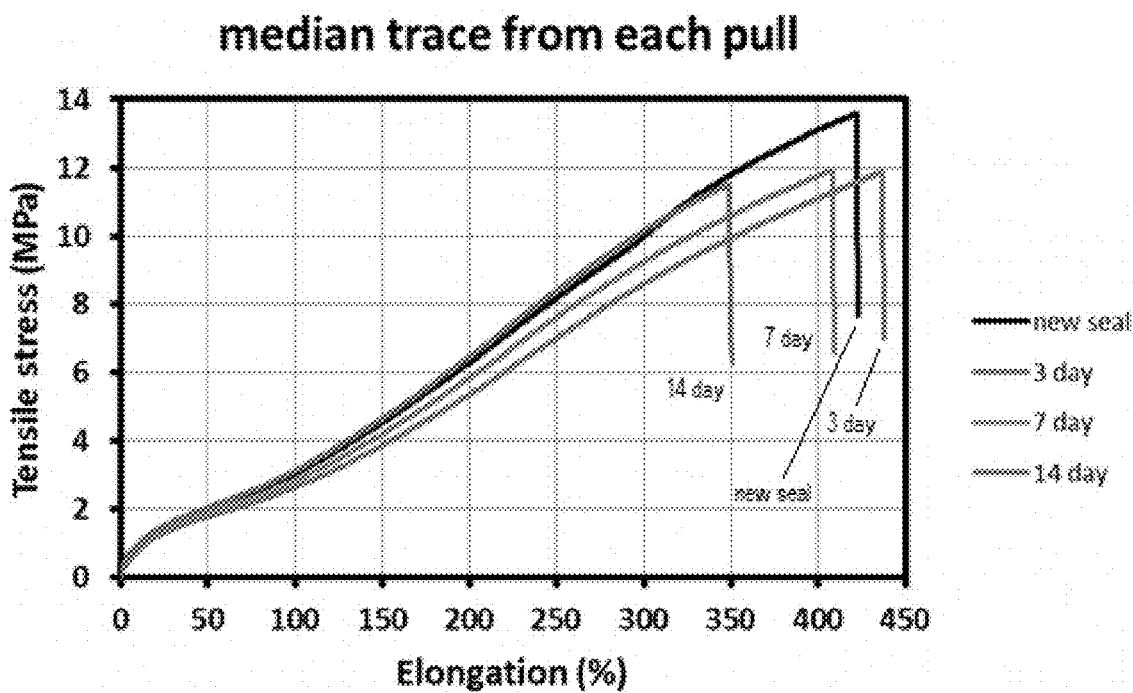
Figure 4:
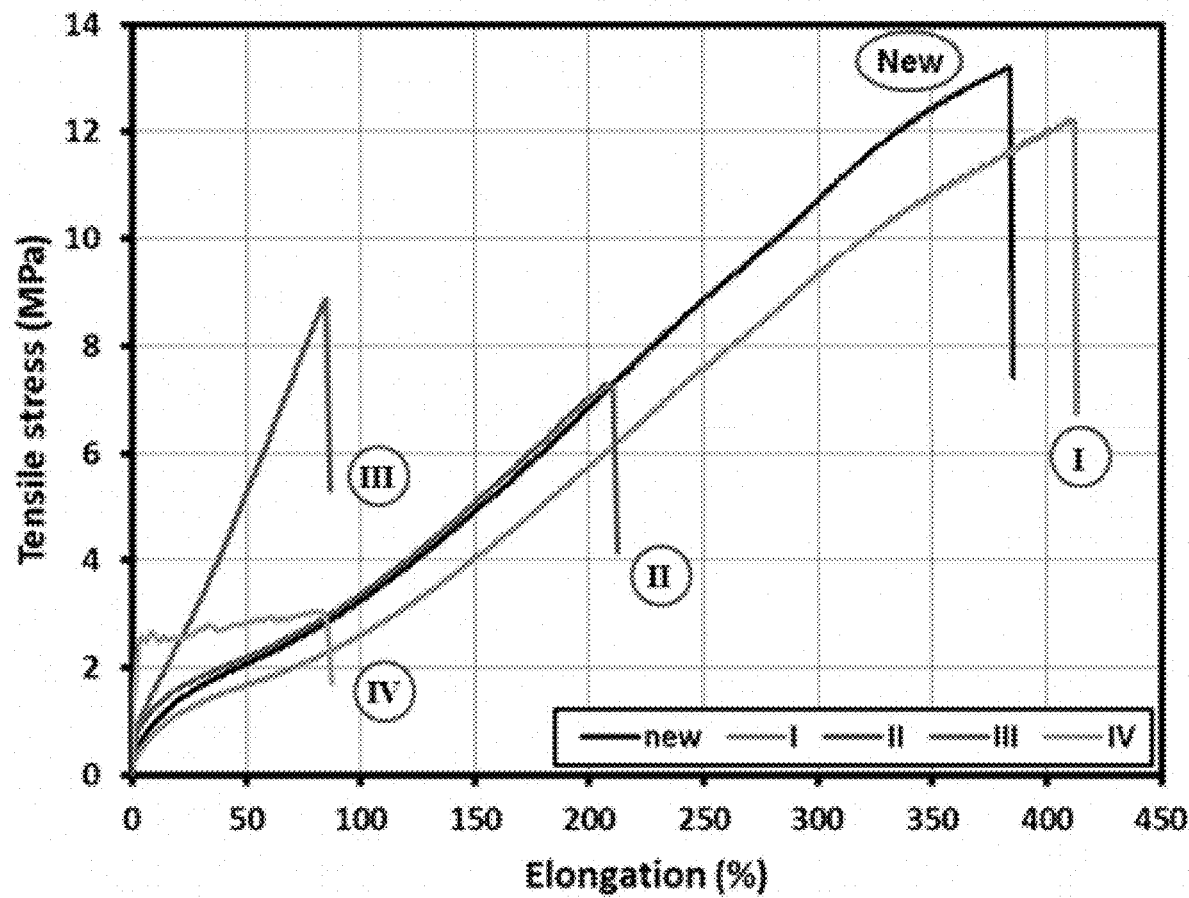
FIG. 4 is a plot of 14-day stress-strain curves.

FIGS. 3a and 3b show the effect of 0.20 wt % of Irgamet® 39 and 0.89 wt % of Compound 1, respectively (c.f. the 14 day stress-strain curves in FIG. 4 (provided here for reference purposes) which demonstrate different types of failure relative to a new elastomer). With Irgamet® 39 it can be seen that within 3 days significant loss of tensile properties, both tensile strength and elongation, was seen, as well as a significant increase in hardness. The significant increase in hardness indicates a crosslinking mechanism. However, with Compound 1 it can be seen that almost no loss of elongation occurred within 7 days, and only minor loss of elongation occurred at 14 days. Hardness does not increase to any significant amount indicating that the crosslinking mechanism has been shut down.

Example 3—Fluoropolymer Seal Compatibility Testing of Compound 1 vs Irgamet®

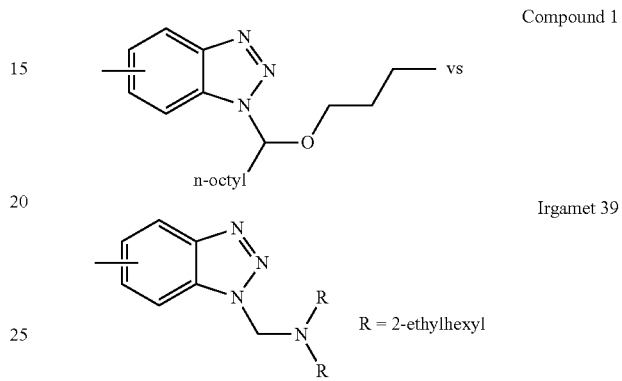

Compound 1 (1-[1-(butyloxy)octyl]toluyltriazole) and Irgamet® 39 were compared in the presence of other additives to simulate a fully formulated hydraulic fluid (see Fluids 1-3).

Thus, three hydraulic fluids referred to below as Fluids 1 to 3 with the compositions given in Table 3 were prepared. Fluids 1 and 2 contained Compound 1 as the sole corrosion inhibitor (in differing amounts), whereas Fluid 3 contained Irgamet® 39 as the sole corrosion inhibitor (whose % N is equivalent to the triazole compound in Fluid 2). Each of Fluids 1 to 3 also included (in addition to the components that are identified below in Table 3) 6% of a viscosity modifier; 0.3% of a pour point depressant; 0.2% of a combination of phenolic and aminic antioxidants; minor amounts (≤0.1% each) of a sulfonate rust inhibitor, a solubilizer, a Ca phenate detergent, a demulsifier, some $C_8$-alcohol solvent, and a defoamant (with the same additives being used in each case); with the balance being base oil.

TABLE 3

(all amounts in weight %)

|  | Fluid 1 | Fluid 2 | Fluid 3 |
|---|---|---|---|
| Irgamet ® 39 - amount in wt. % | — | — | 0.08 |
| Compound 1 - amount in wt % | 0.03 | 0.08 | — |
| wt. % N from triazole compound | 0.003 | 0.01 | 0.01 |
| Dispersant 1 | 0.36 | 0.36 | 0.36 |
| Anti-wear agent 1 (AW1) | 0.04 | 0.04 | 0.04 |
| Anti-wear agent 2 (AW2) | 0.10 | 0.10 | 0.10 |

Dispersant 1=PIB succinimide made from PIB having a number average molecular weight of around 950

AW1: ashless alkyl dithiophosphate acid: $(^iBuO)_2P(=S)S-CH_2-CH(CH_3)-CO_2H$

AW2: ashless alkyl dithiophosphate ester: $(^iPrO)_2P(=S)S-CH_2-CH_2-CO_2R$ where $R=C_{2-5}$ Each of Fluids 1 to 3 was subjected to fluoropolymer seal compatibility testing. Samples of FKM fluoropolymer material were immersed in the hydraulic fluid for a defined period of time and at a specific temperature. The samples were then analysed. An improvement in fluoropolymer seal compatibility may be evidenced by one or more of, an increase in tensile strength, an increase in elongation at break, or a reduction in the change in hardness. The results are set out below in Table 4

TABLE 4

FKM seal compatibility scores for Fluids 1-3 in RFT-EC-Rexroth-Fluid-Test-Elastomer-Compatibility HLP/HVLP/HEPR, using 75 FKM 595 seals.

| Property | Tolerance limits | 1 | 2 | 3 |
|---|---|---|---|---|
| Change in volume | (−)3/5 | −0.6 | −0.5 | 1.0 |
| Change in weight | (−)2/3 | −0.4 | −0.2 | 0.5 |
| Change in hardness | 10/(−)5 | 5 | 5 | 7 |
| Tensile strength | >8 | 9 | 9 | 8.3 |
| Change in median (Tensile strength) | 50/(−)25 | −9 | −9 | −23 |
| Elongation at break | >100 | 126 | 119 | 74 |
| Change in median (Elongation at break) | 30/(−)65 | −66 | −67 | −77 |
| Stress at 100% elongation | N/A | 8.2 | 8.4 | −* |
| Change in median (Stress at 100% elongation) | 125/(−)30 | 64 | 67 | −* |

*unable to measure when Elongation at break is less than 100.

Fluid 3, which contained Irgamet® 39 in a relatively low amount, failed the FKM seal compatibility test (see the elongation at break and tensile strength results for Fluid 3). These results reflect the aggressive nature of the test (1008 H at 130° C.), which in turn reflects the increasingly high standards required in modern hydraulic systems in terms of seal compatibility. The Fluids containing Compound 1 in varying amounts met the criteria to meet the FKM seal compatibility test (one failing parameter is acceptable). Both passed the FKM seal compatibility test, even including the one with an equivalent wt. % N.

Example 4—Fluoropolymer Seal Compatibility Testing of Compound 2 vs Irgamet®

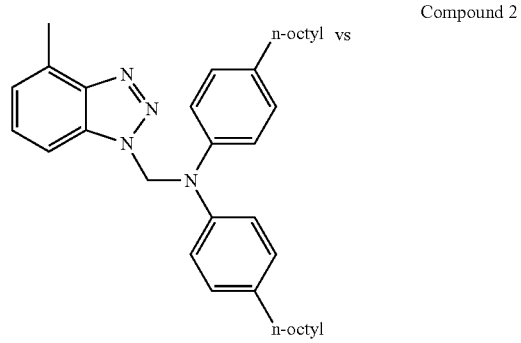

Compound 2

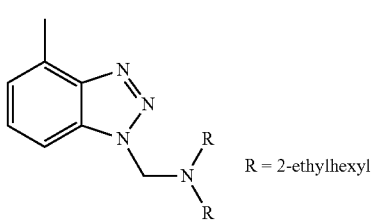

Irgamet 39
R = 2-ethylhexyl

Compound 2 (1-[di(4-octylphenyl)aminomethyl]toluyl-triazole) and Irgamet® 39 were compared in the presence of other additives to simulate a fully formulated hydraulic fluid (see Fluids 1-4) and also in the absence of other additives (see Fluids 5-10).

Thus, firstly, four hydraulic fluids referred to below as Fluids 1 to 4 with the compositions given in Table 5 were prepared. Fluids 1 to 3 contained Compound 2 as the sole corrosion inhibitor (in differing amounts), whereas Fluid 4 contained Irgamet® 39 as the sole corrosion inhibitor (in a molar amount which lies between the molar amount of the triazole compound in Fluids 1 and 2). Each of Fluids 1 to 4 also included (in addition to the components that are identified below in Table 4) 6% of a viscosity modifier; 0.3% of a pour point depressant; 0.2% of a combination of phenolic and aminic antioxidants; minor amounts (≤0.1% each) of a sulfonate rust inhibitor, a solubilizer, a Ca phenate detergent, a demulsifier, some $C_8$-alcohol solvent, and a defoamant (with the same additives being used in each case); with the balance being base oil.

TABLE 5

(all amounts in weight %)

| | Fluid 1 | Fluid 2 | Fluid 3 | Fluid 4 |
|---|---|---|---|---|
| Irgamet ®39 - amount in wt % | — | — | — | 0.08 |
| Compound 2 - amount in wt. % | 0.13 | 0.09 | 0.04 | — |
| % N of the triazole | 0.013 | 0.009 | 0.004 | 0.01 |
| Dispersant 1 | 0.36 | 0.36 | 0.36 | 0.36 |
| Anti-wear agent 1 (AW1) | 0.04 | 0.04 | 0.04 | 0.04 |
| Anti-wear agent 2 (AW2) | 0.10 | 0.10 | 0.10 | 0.10 |

Dispersant 1=PIB succinimide made from PIB having a number average molecular weight of around 950

AW1: ashless alkyl dithiophosphate acid: $(^iBuO)_2P(=S)S-CH_2-CH(CH_3)-CO_2H$

AW2: ashless alkyl dithiophosphate ester: $(^iPrO)_2P(=S)S-CH_2-CH_2-CO_2R$ where $R=C_{2-5}$ And then secondly, six further fluids (labelled Fluids 5 to 10) were prepared as solutions of single component systems of Compound 2 or Irgamet® 39 in base oil. The compositions are set out in Table 6 below.

TABLE 6

(all amounts in wt %)

| | Fluid 5 | Fluid 6 | Fluid 7 | Fluid 8 | Fluid 9 | Fluid 10 |
|---|---|---|---|---|---|---|
| Amount of Irgamet ® 39 in wt % | — | — | — | — | — | 0.08 |
| Compound 2 - amount in wt % | 0.13 | 0.09 | 0.04 | 0.02 | 0.01 | — |
| % N of the triazole | 0.013 | 0.009 | 0.004 | 0.002 | 0.001 | 0.01 |

Each of Fluids 1 to 10 was subjected to fluoropolymer seal compatibility testing. Samples of FKM fluoropolymer material were immersed in the hydraulic fluid for a defined period of time and at a specific temperature. The samples were then analysed. An increase in fluoropolymer seal compatibility may be evidenced by one or more of, an increase in tensile strength, an increase in elongation at break or a reduction in the change in hardness. The results are set out below in Tables 7 and 8.

Table 7—FKM seal compatibility scores for Fluids 1-4 in RFT-EC-Rexroth-Fluid-Test-Elastomer-Compatibility HLP/HVLP/HEPR, using 75 FKM 595 seals.

For Fluids 1-3, scores are reported as the average over two test runs. For Fluid 4, scores are reported as the average over three test runs.

| Property | Tolerance limits | Fluid 1 | Fluid 2 | Fluid 3 | Fluid 4 |
|---|---|---|---|---|---|
| Change in volume | (−)3/5 | 0.1 | 0.0 | −0.5 | 1.0 |
| Change in weight | (−)2/3 | 0.2 | 0.0 | −0.2 | 0.5 |
| Change in hardness | 10/(−)5 | 8 | 6 | 6 | 7 |
| Tensile strength | >8 | 9.5 | 9.5 | 9.9 | 8.3 |
| Change in median (Tensile strength) | 50/(−)25 | 1 | 1 | 5 | −23 |
| Elongation at break | >100 | 107 | 124 | 137 | <u>74</u> |
| Change in median (Elongation at break) | 30/(−)65 | <u>−66</u> | −61 | −56 | <u>−77</u> |
| Stress at 100% elongation | N/A | 9.2 | 8.4 | 7.3 | −* |
| Change in median (Stress at 100% elongation) | 125/(−)30 | 79 | 64 | 62 | −* |

*Unable to measure if Elongation at break is less than 100.

TABLE 8

FKM seal compatibility scores for Fluids 5-10 in RFT-EC-Rexroth-Fluid-Test-Elastomer-Compatibility HLP/HVLP/HEPR, using 75 FKM 595 seals.

| Property | Tolerance limits | Fluid 5 | Fluid 6 | Fluid 7 | Fluid 8 | Fluid 9 | Fluid 10 |
|---|---|---|---|---|---|---|---|
| Change in volume | (−)3/5 | 0.7 | 0.5 | 0.6 | 0.2 | 0.3 | 0.2 |
| Change in weight | (−)2/3 | 0.3 | 0.2 | 0.1 | 0 | −0.1 | 0.2 |
| Change in hardness | 10/(−)5 | 2 | 1 | 1 | 0 | 0 | 6 |
| Tensile strength | >8 | 12 | 12.1 | 11.7 | 11.4 | 11.5 | <u>6.6</u> |
| Change in median (Tensile strength) | 50/(−)25 | 17 | 18 | 14 | 11 | 12 | −18 |
| Elongation at break | >100 | 242 | 260 | 268 | 278 | 276 | 103 |
| Change in median (Elongation at break) | 30/(−)65 | −22 | −16 | −14 | −11 | −11 | <u>−70</u> |
| Stress at 100% elongation | N/A | 7.5 | 7.5 | 6.8 | 6.7 | 6.6 | 6.4 |
| Change in median (Stress at 100% elongation) | 125/(−)30 | 27 | 27 | 14 | 13 | 11 | 51 |

Fluids 4 and 10, which contained Irgamet® 39 in a relatively low amount, failed the FKM seal compatibility test (see the elongation at break result for Fluid 4 and the tensile strength result for Fluid 10). These results reflect the aggressive nature of the test (1008 H at 130° C.), which in turn reflects the increasingly high standards required in modern hydraulic systems in terms of seal compatibility. The Fluids containing Compound 2 in varying amounts all passed the FKM seal compatibility test, even including those which had a greater molar amount of the triazole compound.

Example 5—Copper Passivation Testing for Compound 1 vs Irgamet® 39

Fluids 1 to 3 as described in Table 3 above were tested according to the standard tests set out below. The copper corrosion test results are set out beneath that in Table 9.
 (a) ASTM D130: Standard Test Method for Corrosiveness to Copper from Petroleum Products by Copper Strip Test.
 (b) ASTM D2619: Standard Test Method for Hydrolytic Stability of Hydraulic Fluids.
 (c) ASTM D2272: Standard Test Method for Oxidation Stability of Steam Turbine Oils by Rotating Pressure Vessel.
 (d) ASTM D665: Standard Test Method for Rust-Preventing Characteristics of Inhibited Mineral Oil in the Presence of Water.
 (e) ASTM D4310: Standard Test Method for Determination of Sludging and Corrosion Tendencies of Inhibited Mineral Oils.

TABLE 9

Copper passivation data

| | Fluid 1 | Fluid 2 | Fluid 3 |
|---|---|---|---|
| ASTM D130 (3 h/100° C.) | 1A | 1A | 1A |
| ASTM D130 (3 h/121° C.) | 1A | 1A | 1B |
| ASTM D2169 | | | |
| Copper weight loss/mg | 0.02 | 0.01 | 0.09 |
| Acidity of water/mgKOH | 0 | 0 | 0 |
| Appearance of copper strip | 1B | 1B | 1B |
| ASTM D2272/minutes (Duplicate) | 148* | 245* | 436* |
| ASTM D665 B (Duplicate) | Pass/Pass | Pass/Pass | Pass/Pass |
| ASTM D4310 | | | |
| Weight of total copper/mg | 16.1* | 9.6* | 5.8 |
| Weight of total iron/mg | 0.1* | 0.2* | 0.5 |

Scores marked * are averages across two test runs (other scores are for single test runs)

Although the scores vary for Fluids 1-3, all scores are passing in the copper corrosion tests. Fluid 3 which contains Irgamet® 39 in a relatively low amount is able to provide satisfactory corrosion inhibition but (as noted above in Example 3) failed the FKM seal compatibility test. Fluids 1 and 2 contain varying amounts of Compound 1 as the sole corrosion inhibitor. Each of Fluids 1 and 2 provided robust performance in terms of both corrosion inhibition (e.g. compare the ASTM D2619 copper weight loss of just 0.02 mg, 0.01 mg, and 0.01 mg respectively, as compared to 0.09 mg for Fluid 3 which contains Irgamet® 39) and seal compatibility (see Example 3 above).

It is noteworthy that Fluid 2 is able to achieve both strong corrosion inhibition and good seal compatibility in the context of fluids containing a series of further additives—including, among others, detergent, dispersant, phosphate anti-wear and antioxidant additives (which will impart further properties to the fluid). This illustrates how the surprising effectiveness of the corrosion inhibiting agent of the present invention allows the formulation of fluoropolymer seal compatible fluids offering an advantageous balance of desirable properties.

Example 6—Copper Passivation Testing for Compound 2 vs Irgamet® 39

Fluids 1-4 as described above in Table 5 were tested according to the standard tests set out below. The copper corrosion test results are set out beneath that in Table 10.
 (a) ASTM D130: Standard Test Method for Corrosiveness to Copper from Petroleum Products by Copper Strip Test.
 (b) ASTM D2619: Standard Test Method for Hydrolytic Stability of Hydraulic Fluids.
 (c) ASTM D2272: Standard Test Method for Oxidation Stability of Steam Turbine Oils by Rotating Pressure Vessel.

(d) ASTM D665: Standard Test Method for Rust-Preventing Characteristics of Inhibited Mineral Oil in the Presence of Water.
(e) ASTM D4310: Standard Test Method for Determination of Sludging and Corrosion Tendencies of Inhibited Mineral Oils.

TABLE 10

Copper passivation data

|  | Fluid 1 | Fluid 2 | Fluid 3 | Fluid 4 |
|---|---|---|---|---|
| ASTM D130 (3 h/100° C.) | 1A | 1A | 1A | 1A |
| ASTM D130 (3 h/121° C.) | 1A | 1A | 1A | 1B |
| ASTM D2169 |  |  |  |  |
| Copper weight loss/mg | 0 | 0.01 | 0.01 | 0.09 |
| Acidity of water/mgKOH | 0 | 0 | 0 | 0 |
| Appearance of copper strip | 1B | 1B | 1B | 1B |
| ASTM D2272/minutes |  |  |  |  |
| (Duplicate) | 990* | 808* | 380* | 436* |
| ASTM D665 B (Duplicate) | Pass/Pass | Pass/Pass | Pass/Pass | Pass/Pass |
| ASTM D4310 |  |  |  |  |
| Weight of total copper/mg | 5.8* | 13.3* | 23.5* | 5.8 |
| Weight of total iron/mg | 1.2* | 0.7* | 0.4* | 0.5 |

Scores marked * are averages across two test runs (other scores are for single test runs)

Fluids 1-4 all pass the Copper corrosion tests. Fluid 4 which contains Irgamet® 39 in a relatively low amount is able to provide satisfactory corrosion inhibition but (as noted above in Example 4) failed the FKM seal compatibility test. Fluids 1-3 contain varying amounts of Compound 2 as the sole corrosion inhibitor. Each of Fluids 1-3 provided robust performance in terms of both corrosion inhibition (e.g. compare the ASTM D2619 copper weight loss of just 0 mg, 0.01 mg, and 0.01 mg respectively, as compared to 0.09 mg for Fluid 4 which contains Irgamet® 39) and seal compatibility (see Example 4 above).

It is noteworthy that Fluid 2 is able to achieve both strong corrosion inhibition and good seal compatibility in the context of fluids containing a series of further additives—including, among others, detergent, dispersant, phosphate anti-wear and antioxidant additives (which will impart further properties to the fluid). This illustrates how the surprising effectiveness of the corrosion inhibiting agent of the present invention allows the formulation of fluoropolymer seal compatible fluids offering an advantageous balance of desirable properties.

It can be seen from the above results that using Compound 1 or Compound 2 affords a surprisingly improved balance of properties when it comes to the potentially competing goals of good functionality (such as good corrosion inhibition) and good fluoropolymer seal compatibility.

Below are now provided a series of numbered clauses [1] to [28] defining preferred embodiments of the invention. These numbered clauses are not the claims (the claims appear further below, in separate section titled "CLAIMS").

[1] A hydraulic fluid comprising:
(a) 40 to 2000 ppm by weight in terms of nitrogen content of a corrosion inhibiting agent which is one or more compounds of formula (I):

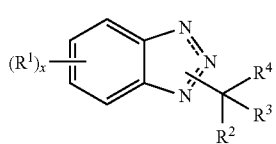

and/or tribologically acceptable salts thereof, wherein in formula (I):
each $R^1$ is independently a hydrocarbyl group comprising 1 to 10 carbon atoms,
x is 0 to 4,
each of $R^2$ and $R^3$ is independently hydrogen or a hydrocarbyl group comprising 1 to 20 carbon atoms,
$R^4$ is —$NR^5R^6$ or —$OR^7$,
each of $R^5$ and $R^6$ is independently an aryl group comprising 6 to 14 carbon atoms, optionally substituted with one or more hydrocarbyl groups comprising 1 to 20 carbon atoms,
$R^7$ is a hydrocarbyl group comprising 1 to 20 carbon atoms, and
in each of said hydrocarbyl groups containing 2 or more carbon atoms, the carbon chain may, independently, optionally be interrupted by one or more ether groups;
(b) 0.1 to 1% by weight of an ashless nitrogen-containing dispersant; and
(c) a major amount of a base oil.

[2] A hydraulic fluid according to [1] wherein $R^4$ is —$NR^5R^6$ and the amount of said one or more compounds of formula (I) and/or tribologically acceptable salts thereof is 50 to 200 ppm by weight in terms of nitrogen content.

[3] A hydraulic fluid according to [1] or [2], wherein:
each $R^1$ is independently a straight or branched alkyl group comprising 1 to 4 carbon atoms, and preferably is methyl,
x is 0 or 1,
$R^2$ is hydrogen or a straight or branched alkyl group comprising 1 to 4 carbon atoms, and preferably is hydrogen,
$R^3$ is hydrogen or a straight or branched alkyl group comprising 1 to 4 carbon atoms, and preferably is hydrogen,
$R^4$ is —$NR^5R^6$, and
each of $R^5$ and $R^6$ is independently a phenyl group substituted with a hydrocarbyl group comprising 6 to 10 carbon atoms.

[4] A hydraulic fluid according to [1] wherein $R^4$ is —$OR^7$ and the amount of said one or more compounds of formula (I) and/or tribologically acceptable salts thereof is 40 to 150 ppm by weight in terms of nitrogen content.

[5] A hydraulic fluid according to [1] or [4], wherein:
each $R^1$ is independently a straight or branched alkyl group comprising 1 to 4 carbon atoms, and preferably is methyl,
x is 0 or 1,
$R^1$ is a straight or branched alkyl group comprising 4 to 12 carbon atoms, and preferably 6 to 10 carbon atoms,
$R^3$ is hydrogen or a straight or branched alkyl group comprising 1 to 4 carbon atoms, and preferably is hydrogen,
$R^4$ is —$OR^7$, and
$R^7$ is a straight or branched alkyl group comprising 2 to 8 carbon atoms, and preferably 3 to 6 carbon atoms.

[6] A hydraulic fluid according to any one of [1] to [5], wherein the ashless dispersant is present in an amount of 1500 to 4000 ppm by weight, and is a nitrogen-containing ashless dispersant, and preferably is a succinimide.

[7] A hydraulic fluid according to any one of [1] to [6], which further comprises one or more phosphate anti-wear agents, wherein the total amount of said one or more phosphate anti-wear agents is 100 to 3000 ppm by weight, and wherein preferably said one or more phosphate anti-wear agents is free from zinc.

[8] A hydraulic fluid according to any one of [1] to [7], which further comprises one or more alkaline earth metal detergents selected from phenate detergents, substituted benzene sulfonate detergents, and salicylate detergents, wherein the total amount of said one or more alkaline earth metal detergents is 50 to 2000 ppm by weight.

[9] A hydraulic fluid according to any one of [1] to [8], which further comprises one or more antioxidants, preferably a phenolic antioxidant and/or an amine antioxidant.

[10] A hydraulic fluid according to any one of [1] to [9], which further comprises a rust inhibitor in an amount of 100 to 2000 ppm, wherein preferably said rust inhibitor is an aryl sulfonate salt.

[11] A hydraulic fluid according to any one of [1] to [10], which further comprises a demulsifier, preferably a non-ionic surfactant such as a block copolymer terminating in hydroxyl groups.

[12] A hydraulic fluid according to any one of [1] to [11], which further comprises a viscosity modifier and/or a pour point depressant.

[13] An additive concentrate comprising:
(a) 2.0 to 20% by weight of a corrosion inhibiting agent which is one or more compounds of formula (I):

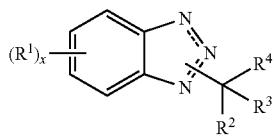

and/or tribologically acceptable salts thereof, wherein in formula (I):
each $R^1$ is independently a hydrocarbyl group comprising 1 to 10 carbon atoms,
x is 0 to 4,
each of $R^2$ and $R^3$ is independently hydrogen or a hydrocarbyl group comprising 1 to 20 carbon atoms,
$R^4$ is —$NR^5R^6$ or —$OR^7$,
each of $R^5$ and $R^6$ is independently an aryl group comprising 6 to 14 carbon atoms, optionally substituted with one or more hydrocarbyl groups comprising 1 to 20 carbon atoms,
$R^7$ is a hydrocarbyl group comprising 1 to 20 carbon atoms, and
in each of said hydrocarbyl groups containing 2 or more carbon atoms, the carbon chain may, independently, optionally be interrupted by one or more ether groups;
(b) 11 to 50% by weight of an ashless nitrogen-containing dispersant; and optionally
(c) a diluent.

[14] An additive concentrate according to [13] wherein $R^4$ is —$NR^5R^6$ and the amount of said one or more compounds of formula (I) and/or tribologically acceptable salts thereof is 3.0 to 14% by weight.

[15] An additive concentrate according to [13] or [14] wherein
each $R^1$ is independently a straight or branched alkyl group comprising 1 to 4 carbon atoms, and preferably is methyl,
x is 0 or 1, $R^2$ is hydrogen or a straight or branched alkyl group comprising 1 to 4 carbon atoms, and preferably is hydrogen,
$R^3$ is hydrogen or a straight or branched alkyl group comprising 1 to 4 carbon atoms, and preferably is hydrogen,
$R^4$ is —$NR^5R^6$, and
each of $R^5$ and $R^6$ is independently a phenyl group substituted with a hydrocarbyl group comprising 6 to 10 carbon atoms.

[16] An additive concentrate according to [13] wherein $R^4$ is —$OR^7$ and the amount of said one or more compounds of formula (I) and/or tribologically acceptable salts thereof is 2.0 to 9.0% by weight.

[17] An additive concentrate according to [13] or [16] wherein:
each $R^1$ is independently a straight or branched alkyl group comprising 1 to 4 carbon atoms, and preferably is methyl,
x is 0 or 1,
$R^1$ is a straight or branched alkyl group comprising 4 to 12 carbon atoms, and preferably 6 to 10 carbon atoms,
$R^3$ is hydrogen or a straight or branched alkyl group comprising 1 to 4 carbon atoms, and preferably is hydrogen,
$R^4$ is —$OR^7$, and
$R^7$ is a straight or branched alkyl group comprising 2 to 8 carbon atoms, and preferably 3 to 6 carbon atoms.

[18] An additive concentrate according to any one of [13] to [17], wherein the ashless nitrogen-containing dispersant is a product obtainable from the reaction of (a) an amino compound, with (b) succinic acid and/or succinic anhydride substituted by a hydrocarbyl group having a number average molecular weight of at least 300, and preferably 900 to 1200, wherein said reaction involves the formation of at least one imido, amido, amidine, and/or acyloxy ammonium linkage, wherein the product is substituted by a hydrocarbyl group having a number average molecular weight of at least 300, and preferably 900 to 1200.

[19] An additive concentrate according to any one of [13] to [18], wherein the corrosion inhibiting agent is present in an amount of 2.3 to 9.0% by weight, and/or the dispersant is present in an amount of 13 to 45% by weight.

[20] An additive concentrate according to any one of [13] to [19], which further comprises:
(i) one or more metal detergents in an amount of 0.7 to 8.0% by weight;
(ii) one or more phosphate anti-wear agents in an amount of 0.7 to 23% by weight;
(iii) one or more antioxidants in an amount of 3.7 to 37% by weight;
(iv) one or more rust inhibitors in an amount of 0.07 to 15% by weight; and/or
(v) a demulsifier in an amount of 0.007 to 3.7% by weight.

[21] A compound of formula (II):

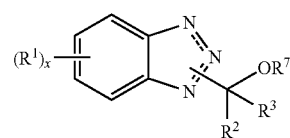

or a tribologically acceptable salt thereof, wherein in formula (II):

each R¹ is independently a hydrocarbyl group comprising 1 to 10 carbon atoms,
x is 0 to 4,
each of R² and R³ is independently hydrogen or a hydrocarbyl group comprising 1 to 20 carbon atoms,
R⁷ is a group comprising 1 to 20 carbon atoms, and
in each of said hydrocarbyl groups containing 2 or more carbon atoms, the carbon chain may, independently, optionally be interrupted by one or more ether groups, provided that either
(a) between them R² and R³ have at least 7 carbon atoms and R⁷ has at least 2 carbon atoms,
(b) between them R² and R³ have at least 5 carbon atoms and R⁷ has at least 2 carbon atoms and is not a cycloalkyl group,
(c) neither of R² and R³ is H, and between them R² and R³ have at least 3 carbon atoms,
(d) x is 1 to 4, R¹ has at least 2 carbon atoms, and either (i) R⁷ has at least 2 carbon atoms, (ii) neither of R² and R³ is H, or (iii) between them R² and R³ have at least 3 carbon atoms, or
(e) x is 2 to 4.
[22] A compound or salt according to [21], wherein:
each R¹ is independently a straight or branched alkyl group comprising 1 to 4 carbon atoms, and preferably is methyl,
x is 0 or 1,
R² is a straight or branched alkyl group comprising 5 to 12 carbon atoms, and preferably 6 to 10 carbon atoms,
R³ is hydrogen or a straight or branched alkyl group comprising 1 to 4 carbon atoms, and preferably is hydrogen, and
R⁷ is a straight or branched alkyl group comprising 2 to 8 carbon atoms, and preferably 3 to 6 carbon atoms.
[23] A hydraulic fluid comprising a compound or salt as defined in [21] or [22], wherein preferably the hydraulic fluid is as defined in any one of [1] to [12].
[24] A hydraulic system comprising at least one fluoropolymer seal and a hydraulic fluid which comes into contact with the seal, wherein the hydraulic fluid is as defined in any one of [1] to [12] or [23].
[25] Use of a hydraulic fluid as defined in any one of [1] to [12] or [23] as a power transmitting fluid.
[26] The use, in a hydraulic fluid, to improve fluoropolymer seal compatibility, or to preserve the integrity of one or more fluoropolymer seals which come into contact with said hydraulic fluid, of 40 to 200 ppm by weight in terms of nitrogen of:
a corrosion inhibiting agent as defined in any one of [1] to [12], or
a compound or salt as defined in [21] or [22].
[27] The use, in a hydraulic fluid, to inhibit corrosion while also (a) improving fluoropolymer seal compatibility, or (b) preserving the integrity of one or more fluoropolymer seals which come into contact with said hydraulic fluid, of 40 to 200 ppm by weight in terms of nitrogen of:
one or more compounds of formula (I) and/or tribologically acceptable salts thereof as defined in any one of [1] to [12], or
a compound or salt as defined in [21] or [22].
[28] A use according to [26] or [27], wherein said hydraulic fluid is as defined in any one of [1] to [12].

The invention claimed is:
1. A hydraulic system comprising at least one fluoropolymer seal and a hydraulic fluid which comes into contact with the seal, wherein the hydraulic fluid comprises:

40 to 2000 ppm by weight in terms of nitrogen content of a corrosion inhibiting agent which is one or more compounds of formula (I):

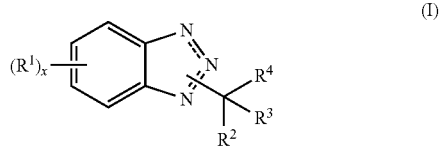

and/or tribologically acceptable salts thereof, wherein in formula (I):
each R¹ is independently a straight or branched alkyl group comprising 1 to 4 carbon atoms,
x is 0 or 1,
each of R² and R³ is independently hydrogen or a straight or branched alkyl group comprising 1 to 4 carbon atoms,
R⁴ is —NR⁵R⁶,
each of R⁵ and R⁶ is independently a phenyl group substituted with a hydrocarbyl group comprising 6 to 10 carbon atoms,
and
in each of said hydrocarbyl groups containing 2 or more carbon atoms, the carbon chain may, independently, optionally be interrupted by one or more ether groups;
0.1 to 1% by weight of an ashless nitrogen-containing dispersant; and
a major amount of a base oil.

2. A hydraulic system according to claim 1 wherein the amount of said one or more compounds of formula (I) and/or tribologically acceptable salts thereof is 50 to 200 ppm by weight in terms of nitrogen content.

3. A hydraulic system according to claim 1, wherein the ashless dispersant is present in an amount of 1500 to 4000 ppm by weight, and is a nitrogen-containing ashless dispersant.

4. A hydraulic system according to claim 1, which further comprises one or more phosphate anti-wear agents, wherein the total amount of said one or more phosphate anti-wear agents is 100 to 3000 ppm by weight.

5. A hydraulic system according to claim 1, which further comprises one or more alkaline earth metal detergents selected from phenate detergents, substituted benzene sulfonate detergents, and salicylate detergents, wherein the total amount of said one or more alkaline earth metal detergents is 50 to 2000 ppm by weight.

6. A hydraulic system according to claim 1, which further comprises one or more antioxidants.

7. A hydraulic system according to claim 1, which further comprises a rust inhibitor in an amount of 100 to 2000 ppm.

8. A hydraulic system according to claim 1, which further comprises a demulsifier.

9. A hydraulic system according to claim 1, which further comprises a viscosity modifier and/or a pour point depressant.

10. A hydraulic system of claim 1, wherein each of R⁵ and R⁶ is independently a phenyl group substituted with a linear hydrocarbyl group comprising 6 to 10 carbon atoms.

11. A hydraulic system of claim 10, wherein the amount of said one or more compounds of formula (I) and/or tribologically acceptable salts thereof is 40 to 120 ppm by weight in terms of nitrogen content.

* * * * *